(12) United States Patent
Saito et al.

(10) Patent No.: US 9,795,783 B2
(45) Date of Patent: Oct. 24, 2017

(54) CONTENT REPRODUCTION APPARATUS, CONTENT REPRODUCTION METHOD, AND STORAGE MEDIUM

(75) Inventors: Naoki Saito, Kanagawa (JP); Yuichiro Mori, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 823 days.

(21) Appl. No.: 13/881,791

(22) PCT Filed: Nov. 9, 2011

(86) PCT No.: PCT/JP2011/075870
§ 371 (c)(1),
(2), (4) Date: Apr. 26, 2013

(87) PCT Pub. No.: WO2012/063883
PCT Pub. Date: May 18, 2012

(65) Prior Publication Data
US 2013/0218067 A1    Aug. 22, 2013

(30) Foreign Application Priority Data

Nov. 9, 2010  (JP) ................................ 2010-251337
Nov. 2, 2011  (JP) ................................ 2011-241721

(51) Int. Cl.
*A61N 1/30*     (2006.01)
*A61N 1/32*     (2006.01)

(52) U.S. Cl.
CPC ............. *A61N 1/303* (2013.01); *A61N 1/325* (2013.01); *A61N 1/30* (2013.01)

(58) Field of Classification Search
CPC .. A61M 2005/14208; A61M 2205/502; A61M 5/1413; A61M 5/1723
(Continued)

(56) References Cited

U.S. PATENT DOCUMENTS 7,749,178 B2    7/2010   Imboden et al.
7,815,582 B2    10/2010  Imboden et al.
(Continued)

FOREIGN PATENT DOCUMENTS

CN    101693137       4/2010
JP    61-036641 U     3/1986
(Continued)

OTHER PUBLICATIONS

Chinese Office Action mailed Jul. 18, 2014.
(Continued)

*Primary Examiner* — Phillip Gray
(74) *Attorney, Agent, or Firm* — IPUSA, PLLC

(57) ABSTRACT

A content reproduction apparatus includes a storage unit storing a plurality of content files and performs treatments by playing the content files stored in the storage unit. The content reproduction apparatus also includes a treatment setting unit configured to set a treatment based on a treatment condition input by a user; a content file obtaining unit configured to obtain, from the storage unit, a content file corresponding to the treatment set by the treatment setting unit; and an edit-and-output unit configured to play the content file obtained by the content file obtaining unit or the content file edited according to an instruction of the user.

14 Claims, 19 Drawing Sheets

(58) Field of Classification Search
USPC .................................................... 604/19–29
See application file for complete search history.

(56) References Cited

U.S. PATENT DOCUMENTS

| | | | |
|---|---|---|---|
| 7,938,789 B2 | 5/2011 | Imboden et al. | |
| 2003/0036683 A1* | 2/2003 | Kehr | G06F 19/325 600/300 |
| 2004/0260212 A1 | 12/2004 | Cho | |

FOREIGN PATENT DOCUMENTS

| | | |
|---|---|---|
| JP | 2002-169574 | 6/2002 |
| JP | 2004-160128 | 6/2004 |
| JP | 2004-209205 | 7/2004 |
| JP | 2005-007164 | 1/2005 |
| JP | 2006-149993 | 6/2006 |
| JP | 2009-039503 | 2/2009 |
| JP | 4217984 | 2/2009 |
| JP | 2009-525130 | 7/2009 |
| JP | 2010-017325 | 1/2010 |
| JP | 3163342 U | 10/2010 |
| WO | WO 2005/035051 | 4/2005 |

OTHER PUBLICATIONS

International Search Report mailed on Dec. 20, 2011.
Japan Office Action mailed Mar. 21, 2012.
Japan Office Action mailed Dec. 4, 2012.
Japan Office Action mailed Mar. 19, 2013.

* cited by examiner

Pass NEGATIVE/POSITIVE

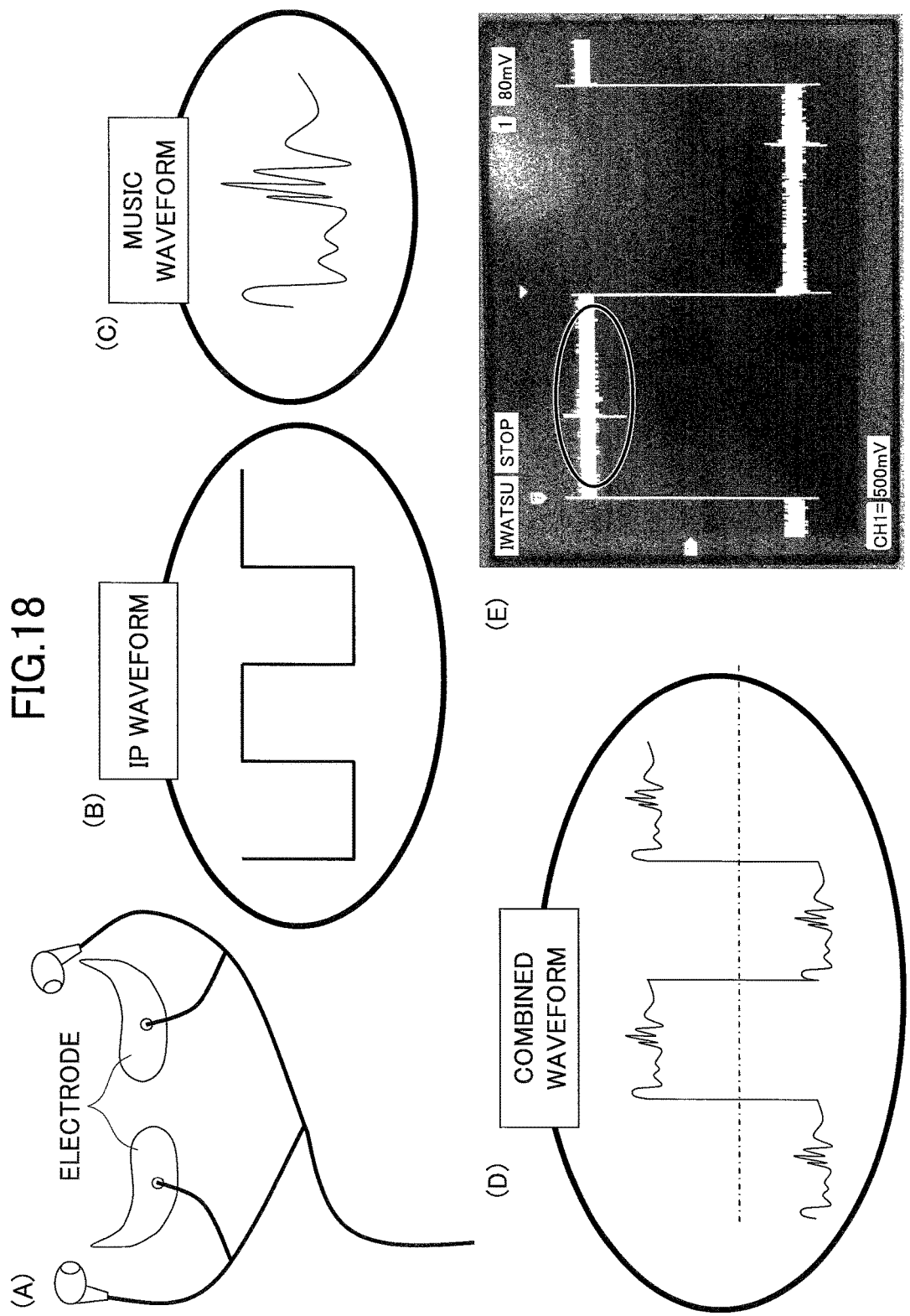

CONTENT REPRODUCTION APPARATUS, CONTENT REPRODUCTION METHOD, AND STORAGE MEDIUM

TECHNICAL FIELD

The present invention relates to a content reproduction apparatus, a content reproduction method, and a storage medium.

BACKGROUND ART

There exists a cosmetic treatment such as iontophoresis where a weak electric current is applied to skin to effectively introduce, for example, water-soluble active ingredients into the skin. The stratum corneum has a barrier function that prevents intrusion of foreign substances. Therefore, for example, when a lotion is simply applied to the skin, water-soluble vitamin C in a lotion is blocked by the barrier function and cannot penetrate into a deep layer of the skin.

Meanwhile, iontophoresis, for example, enables active ingredients of a lotion to pass through a barrier layer and penetrate into a deep layer of skin with the use of electric power.

To receive a cosmetic treatment based on iontophoresis, it is normally necessary to go to a cosmetic clinic or to purchase a cosmetic device dedicated to iontophoresis (see, for example, patent document 1).

There also exists a method for controlling a pulse waveform output from an iontophoretic device depending on the purpose to improve the effect of iontophoresis (see, for example, patent document 2).

RELATED-ART DOCUMENTS

Patent Documents

[Patent document 1] Japanese Patent No. 4217984
[Patent document 2] Japanese Laid-Open Patent Publication No. 2004-209205

DISCLOSURE OF INVENTION

Problems to be Solved by the Invention

However, receiving such a treatment at a cosmetic clinic is very expensive and requires time to visit the cosmetic clinic, and a cosmetic device dedicated to iontophoresis as described in patent document 1 is also expensive. Thus, with the related-art technology, large amounts of money and time are necessary to receive an iontophoresis treatment. Also, with the method disclosed in patent document 2, it is difficult to change or adjust a pulse waveform used for iontophoresis depending on the skin condition of a user.

An aspect of the present invention provides a content reproduction apparatus, a content reproduction method, and a storage medium and makes it possible to easily perform a cosmetic treatment with a widely-used content reproduction apparatus such as a cell phone, a personal computer (PC), a portable device (PD), a personal data assistant (PDA), and a game machine.

Means for Solving the Problems

According to an aspect of the present invention, a content reproduction apparatus includes a storage unit storing a plurality of content files and performs treatments by playing the content files stored in the storage unit. The content reproduction apparatus includes a treatment setting unit configured to set a treatment based on a treatment condition input by a user; a content file obtaining unit configured to obtain, from the storage unit, a content file corresponding to the treatment set by the treatment setting unit; and an edit-and-output unit configured to play the content file obtained by the content file obtaining unit or the content file edited according to an instruction of the user.

Another aspect of the present invention provides a content reproduction method performed by a content reproduction apparatus that includes a storage unit storing a plurality of content files and performs treatments by playing the content files stored in the storage unit. The content reproduction method includes a treatment setting step of setting a treatment based on a treatment condition input by a user; a content file obtaining step of obtaining, from the storage unit, a content file corresponding to the treatment set in the treatment setting step; and an edit-and-output step of playing the content file obtained in the content file obtaining step or the content file edited according to an instruction of the user.

Advantageous Effect of the Invention

An aspect of the present invention makes it possible to easily perform a cosmetic treatment with a widely-used content reproduction apparatus.

BRIEF DESCRIPTION OF THE DRAWINGS

FIG. 18 is a drawing used to describe a method for playing music while performing an iontophoresis treatment.

DESCRIPTION OF EMBODIMENTS

Preferred embodiments of the present invention are described below with reference to the accompanying drawings.

Figure 1:
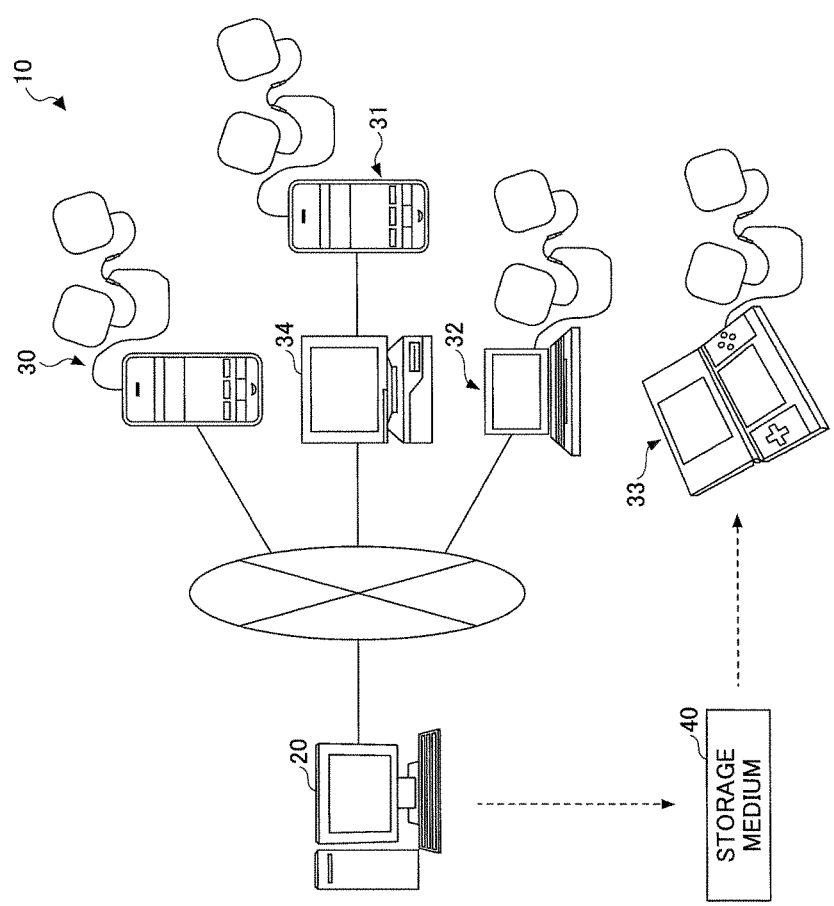
FIG. 1 is a drawing illustrating an exemplary configuration of a content reproduction system according to an embodiment.

FIG. 1 is a drawing illustrating an exemplary configuration of a content reproduction system according to an embodiment of the present invention. As illustrated in FIG. 1, a content reproduction system 10 of the present embodiment includes a content server 20 connected to a communication network such as the Internet and terminal apparatuses 30 through 33 that are examples of content reproduction apparatuses.

The content server 20 stores content files (data) corresponding to various treatments. Examples of the content files include audio files (music files), video files, image files, and text files (e.g., csv files and txt files).

The terminal apparatuses 30 through 33 are content reproduction apparatuses that play or reproduce content files to perform the corresponding cosmetic treatments such as iontophoresis.

The terminal apparatuses 30 through 33 download content files corresponding to treatments to be performed via the communication network from the content server 20.

The terminal apparatus 30 is, for example, a cell phone such as an iPhone (registered trademark) or a smartphone or an information communication terminal such as personal digital assistant (PDA), and can directly download a content file via the communication network.

The terminal apparatus 31 is, for example, a portable device (PD) such as an iPod (registered trademark) and obtains a content file via a PC 34 and the communication network. The terminal apparatus 31 is connected via, for example, a cable to the PC 34 and can obtain a content file corresponding to a treatment to be performed from the PC 34.

The terminal apparatus 32 is, for example, a desktop PC or a notebook PC and can directly obtain a content file via the communication network.

The terminal apparatus 33 is, for example, a game machine and installs a content file from a storage medium 40 such as a Universal Serial Bus (USB) memory, a CD-ROM, a DVD, or an SD card without using the communication network.

With the system configuration described above, the terminal apparatuses 30 through 33 of the present embodiment obtain content files corresponding to treatments to be performed from various types of content files stored in the content server 20. The terminal apparatuses 30 through 33 selectively obtain content files based on cosmetic treatments set in the respective terminal apparatuses 30 through 33 or user (or terminal) identification information.

When the corresponding content files are already in the terminal apparatuses 30 through 33, it is not necessary to obtain the content files from the content server 20.

Figure 2:
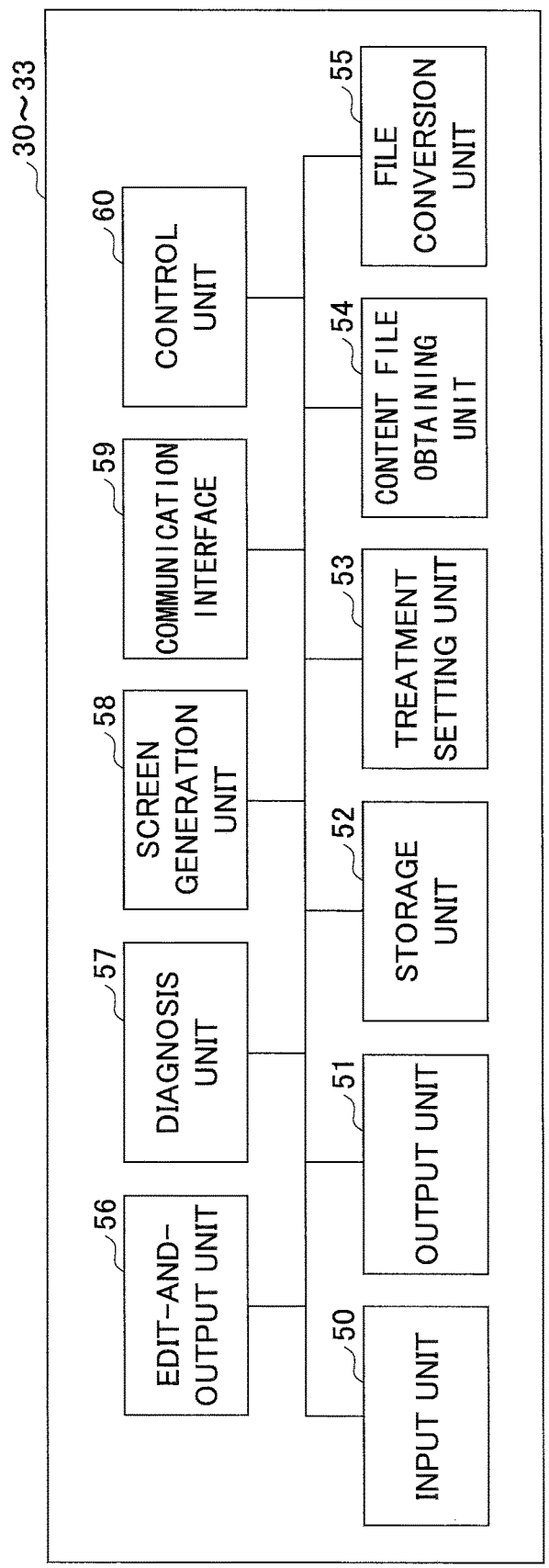
FIG. 2 is a block diagram illustrating an exemplary functional configuration of a content reproduction apparatus.

Next, an exemplary functional configuration of each of the terminal apparatuses 30 through 33, i.e., content reproduction apparatuses, is described. FIG. 2 is a block diagram illustrating an exemplary functional configuration of a content reproduction apparatus.

As illustrated in FIG. 2, each of the terminal apparatuses 30 through 33 includes an input unit 50, an output unit 51, a storage unit 52, a treatment setting unit 53, a content file obtaining unit 54, a file conversion unit 55, an edit-and-output unit 56, a diagnosis unit 57, a screen generation unit 58, a communication interface 59, and a control unit 60.

The input unit 50 is implemented by, for example, operation keys of a cell phone or a keyboard and a pointing device such as a mouse of a PC. The input unit 50 receives user instructions, for example, to start and stop a process. The input unit 50 may also be implemented by an audio input terminal such as a microphone terminal.

The output unit 51 includes, for example, a display that displays information input via the input unit 50 and a result of a process performed based on the input information. The output unit 51 also includes an audio output terminal such as an audio terminal or an earphone jack for outputting audio to a speaker or an earphone. The output unit 51 may also include other audio output terminal such as a dock port of a device (e.g., iPhone or iPod) capable of outputting audio to an external speaker and a USB terminal of a PC.

A cosmetic treatment can be performed as described later using one or more audio output terminals such as an audio terminal, a dock port, and a USB terminal. Also, it is possible to perform different cosmetic treatments concurrently using multiple audio output terminals.

The input unit 50 for receiving various instructions and the output unit 51 for displaying input information may be implemented by, for example, a touch panel.

The storage unit 52 stores, for example, content files downloaded from the content server 20, address information such as a URL for accessing the content server 20, user information, treatment information indicating a treatment such as iontophoresis set by the treatment setting unit 53, treatment time, and diagnostic results obtained by the diagnosis unit 57. Also, the storing unit 52 is capable of reading stored data as necessary.

The treatment setting unit 53 set a treatment to be performed based of treatment conditions input via the input unit 50 by, for example, a user.

The content file obtaining unit 54 obtains, from the storage unit 52, a content file corresponding to the treatment set by the treatment setting unit 53. In the present embodiment, it is assumed that content files are audio files generated, for example, by "YAMAHA Wave Editor TWE V2.3.1" and in one or more of audio file formats such as way (WAVE), AIFF, mp3, mp4, WMA, AAC, RealAudio, and MIDI.

When the content file corresponding to the treatment set by the treatment setting unit 53 is not present in the storage unit 52, the content file obtaining unit 54 accesses the content server 20 or the PC 34 to obtain the content file. Also, the content file obtaining unit 54 may obtain the content file corresponding to the set treatment from the storage medium 40.

The content file obtaining unit 54 can obtain audio files such as a way file and text data such as a csv file and a txt file from, for example, the content server 20.

When the content file obtained by the content file obtaining unit 54 is not an audio file but text data such as a csv file or a txt file, the file conversion unit 55 converts the content file into an audio file such as a wav file.

Also, when the content file obtained by the content file obtaining unit 54 is a video file, the file conversion unit 55 can extract only an audio signal from the video file and convert the extracted audio signal into an audio file.

Thus, even when a content file obtained by the content file obtaining unit 54 is not an audio file, the file conversion unit 55 can convert the content file into an audio file that is usable at the terminal apparatus 30 (31, 32, 33).

Further, the file conversion unit 55 can convert an audio file into a file format (e.g., from the WAV format to the mp4 format) that the terminal apparatus 30 (31, 32, 33) can play.

The edit-and-output unit 56 plays and outputs an audio file obtained by the content file obtaining unit 54 or converted by the file conversion unit 55. The edit-and-output unit 56 also edits data of an obtained or converted audio file according to user instructions and plays and outputs the edited content file.

The edit-and-output unit 56 causes an output signal generated by playing the audio file to be output from a cosmetic device connected to an audio output terminal of the terminal apparatus 30 (31, 32, 33). An example of an output signal of an audio file corresponding to a treatment is described later.

According to the present embodiment, a cosmetic treatment such as iontophoresis is performed on a user (or a recipient) by using an output signal output from a cosmetic device connected to the terminal apparatus 30 (31, 32, 33).

In a process of editing data of an audio file, the edit-and-output unit 56 edits or adjusts, for example, the duration, the output intensity, the play speed, and the waveform of the audio file.

Here, adjusting a waveform may indicate changing the type of wave (e.g., a rectangular wave or a sine wave), the duty ratio, the frequency, and/or the polarity of the waveform. For example, when an iontophoresis treatment is to be performed, the polarity of the waveform is changed to match the polarity of a drug to be introduced. That is, when a drug is to be introduced from the positive electrode, a waveform shifted toward the positive side is used. Thus, according to the present embodiment, it is possible to change a waveform to suit a cosmetic treatment to be performed.

Further, the edit-and-output unit 56 changes or adjusts the number of audio files to be played and the order in which the audio files are played. The edit-and-output unit 56 can also change treatments to be performed and change a combination of audio files for different purposes.

Further, the edit-and-output unit 56 may be configured to combine the waveform of an audio file generated for a treatment and the waveform of music or voice guidance and to output the combined waveform.

In the present embodiment, an audio file is downloaded from another apparatus and stored in the terminal apparatus 30 (31, 32, 33), and the stored audio file is played. However, the present invention is not limited to this embodiment. For example, an audio file for a treatment stored in another apparatus may be streamed to the terminal apparatus 30 (31, 32, 33) to send a signal corresponding to a cosmetic device.

The diagnosis unit 57, for example, obtains the condition of a skin of the user after a treatment and compares the obtained condition of the skin with a condition of the skin of the user recorded in the storage unit 52 before the treatment to determine treatment results.

Here, when an output signal generated by playing an audio file is controlled according to a constant voltage method, the output voltage is controlled to match a predetermined voltage level. In this case, when the resistance of skin of the user varies depending on a part of the skin to which a cosmetic device is brought into contact, the resistance of the part of the skin is represented by a change in the electric current.

Because the resistance and capacitance of skin are related to the amount of moisture in the skin, the diagnosis unit 57 can diagnose the skin condition by detecting a change in the electric current using a measurement device connected to an audio input terminal such as an existing microphone jack and by obtaining the resistance and capacitance of the skin based on the detected change in the electric current.

The diagnosis unit 57 may be configured to send the diagnosed skin condition of the user after treatment to the content server 20 and receive treatment results from the content server 20.

The screen generation unit 58, for example, generates screens such as a menu screen used by the user to enter treatment conditions, a display screen used by the user to select a content file corresponding to a desired treatment, a display screen used by the user to start downloading, and a display screen for displaying treatment and diagnosis results.

The communication interface 60 downloads content files from the content server 20.

The control unit 60 controls other components of the terminal apparatus 30 (31, 32, 33) used as a content reproduction apparatus. For example, the control unit 60 causes the content file obtaining unit 54 to obtain a content file corresponding to a set treatment, causes the file conversion unit 55 to convert a file into an audio file, and causes the edit-and-output unit 56 to edit and output an audio file according to instructions entered by the user.

Figure 3:
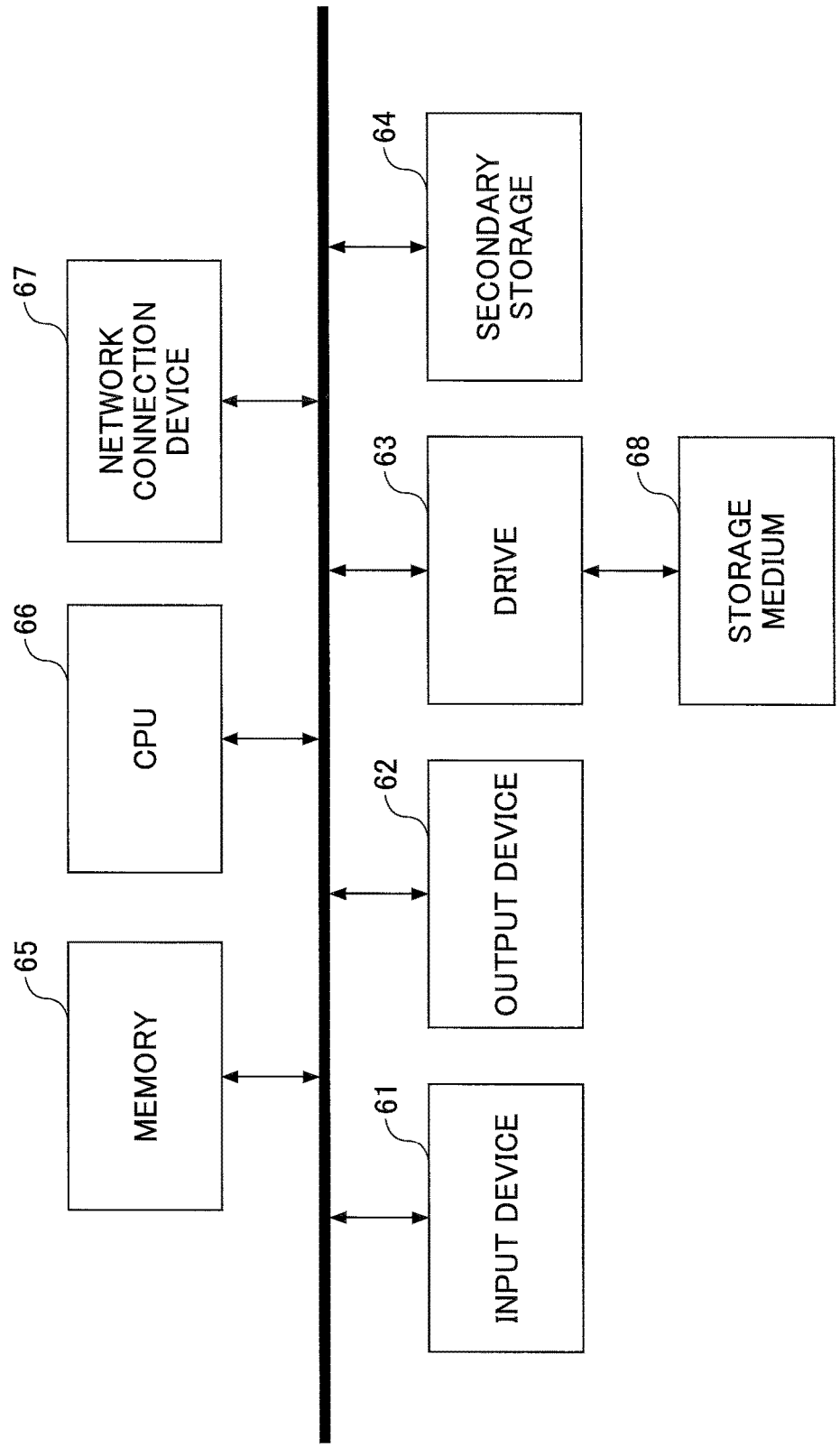
FIG. 3 is a block diagram illustrating an exemplary hardware configuration of a content reproduction apparatus.

An exemplary hardware configuration of each of the terminal apparatuses 30 through 33, which are examples of content reproduction apparatuses, is described below. FIG. 3 is a block diagram illustrating an exemplary hardware configuration of a content reproduction apparatus.

As illustrated in FIG. 3, the content reproduction apparatus includes an input device 61, an output device 62, a drive 63, a secondary storage 64, a memory 65, a central processing unit (CPU) 66, and a network connection device 67 that are connected to each other via a bus B, and a storage medium 68.

The input device 61 may be implemented by a keyboard and a pointing device such as a mouse operated by the user and/or a touch panel operated by the user. The input device 61 is used by the user to enter various instructions such as an instruction to execute a content reproduction program.

The output unit 62 includes a display for displaying various data and windows used to operate a computer to perform processes of the present embodiment. The output unit 62 is controlled by a control program executed by the CPU 66 to display, for example, progress status and processing results of a content reproduction program.

Executable programs including the content reproduction program may be provided in the storage medium 68 such as a CD-ROM. The storage medium 68 is mounted on the drive 63, and the executable programs stored in the storage medium 68 are installed via the drive 63 into the secondary storage 64.

Examples of the storage medium 68 include storage media such as a CD-ROM, a flexible disk, and a magneto-optical (MO) disk that record information optically, electrically, or magnetically, and semiconductor memories such as a ROM and a flash memory that record information electrically.

The secondary storage 64, for example, is a hard disk and stores executable programs such as the content reproduction program, control programs provided for a computer, and various files and data necessary for the execution of the programs. The secondary storage 64 inputs and outputs the programs, files, and data as necessary.

The memory 65 stores, for example, the execution programs retrieved by the CPU 66 from the secondary storage 64. The memory 65 may be implemented by a ROM and/or a RAM.

The CPU 66 performs various calculations and input and output of data from and to other hardware components according to control programs such as an operating system (OS) and the executable programs including the content reproduction program stored in the memory 65, and thereby controls the entire operation of the computer to perform various processes. Information necessary for the execution of programs is obtained from the secondary storage 64 and information generated during the execution of the programs is stored in the secondary storage 64.

The network connection device 67 sends and receives data to and from other terminal apparatuses connected to the terminal apparatus 30 (31, 32, 33) via a communication network or a cable. For example, the network connection device 67 obtains executable programs such as a content reproduction program from other terminal apparatuses, and sends results obtained by executing the programs or the executable programs such as a content reproduction program themselves to other terminal apparatuses.

With the above described hardware configuration, the present embodiment makes it possible to efficiently perform a content reproduction process at a low cost without using special hardware components. Also, the present embodiment makes it possible to use an easily-available apparatus to perform a content reproduction process by installing a program in the apparatus.

Figure 4:
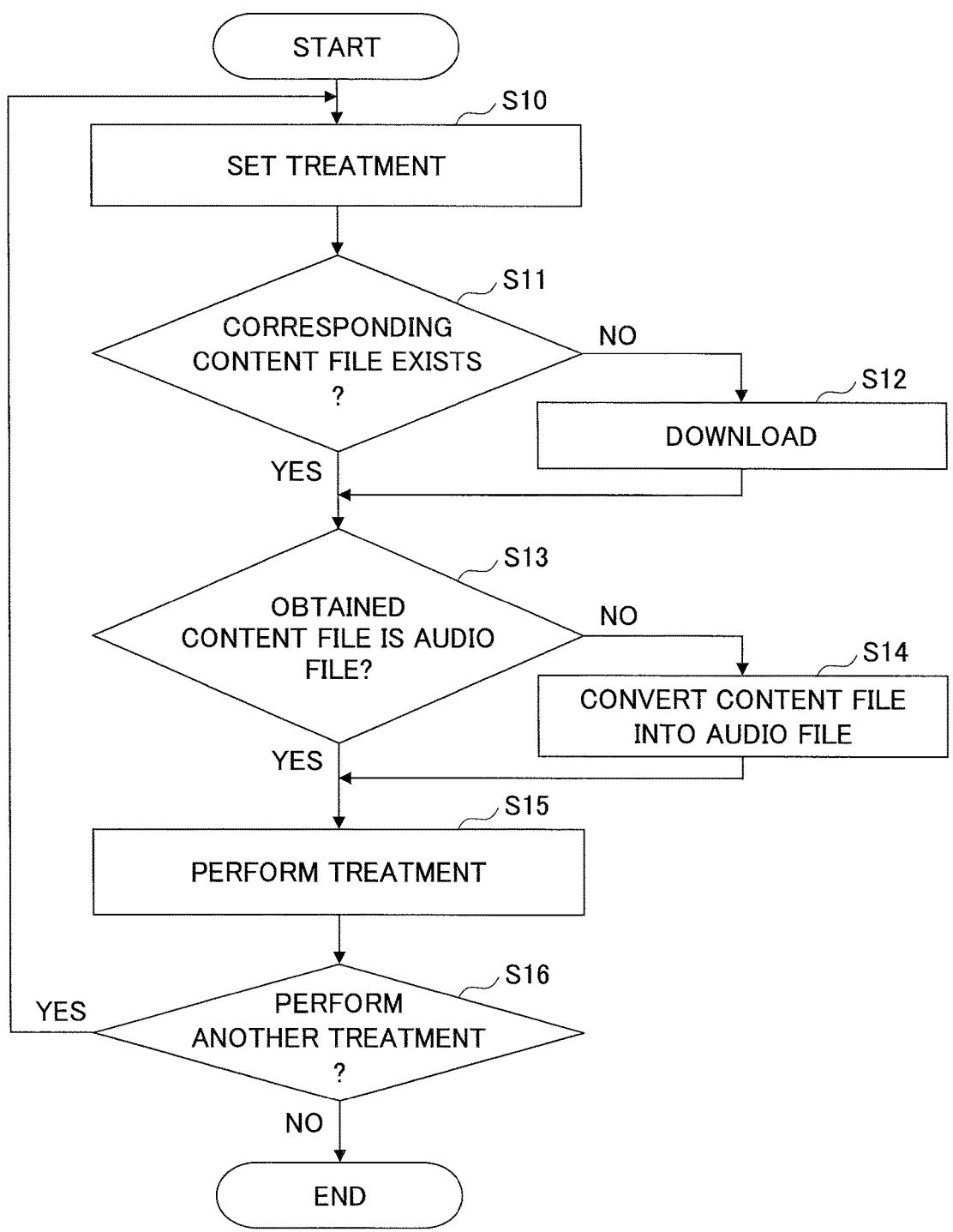
FIG. 4 is a flowchart illustrating a content reproduction process according to an embodiment.

Next, a content reproduction process of the present embodiment is described. FIG. 4 is a flowchart illustrating a content reproduction process according to the present embodiment.

As illustrated in FIG. 4, when the user inputs treatment conditions via, for example, a menu screen of the terminal apparatus 30 (31, 32, 33), the treatment setting unit 53 sets a treatment to be performed based on the input treatment conditions (S10). For example, the treatment conditions input by the user may include a type of cosmetic treatment such as iontophoresis, electrical muscle stimulation (EMS), or a low frequency therapy; conditions (e.g., resistance and capacitance) of skin of the user, and the polarity of a drug.

Next, the content file obtaining unit 54 determines whether a content file corresponding to the treatment set at step S10 exists in the storage unit 52 (S11).

When the content file corresponding to the treatment does not exist in the storage unit 52 (NO at step S11), the content file obtaining unit 54 obtains (or downloads) the content file corresponding to the treatment from the content server 20 (S12).

Meanwhile, when the content file corresponding to the treatment exists in the storage unit 52 (YES at step S11), the content file obtaining unit 54 obtains the content file corresponding to the treatment from the storage unit 52.

Next, the file conversion unit 55 determines whether the content file obtained by the content file obtaining unit 54 is an audio file (S13).

When the obtained content file is not an audio file (NO at step S13), the file conversion unit 55 converts the content file into an audio file (S14).

Meanwhile, when the file conversion unit 55 determines that the obtained content file is an audio file (YES at step S13), the edit-and-output unit 56 plays the audio file to perform the set treatment (S15).

Then, the treatment setting unit 53 determines whether another treatment is performed for the user (S16). When, for example, a corresponding menu button is selected by the user, the treatment setting unit 53 determines that another treatment is performed (YES at step S16) and returns to step S10. Meanwhile, when a quit button is selected by the user, the treatment setting unit 53 determines that another treatment is not performed (NO at step S16) and terminates the process.

Figure 5:
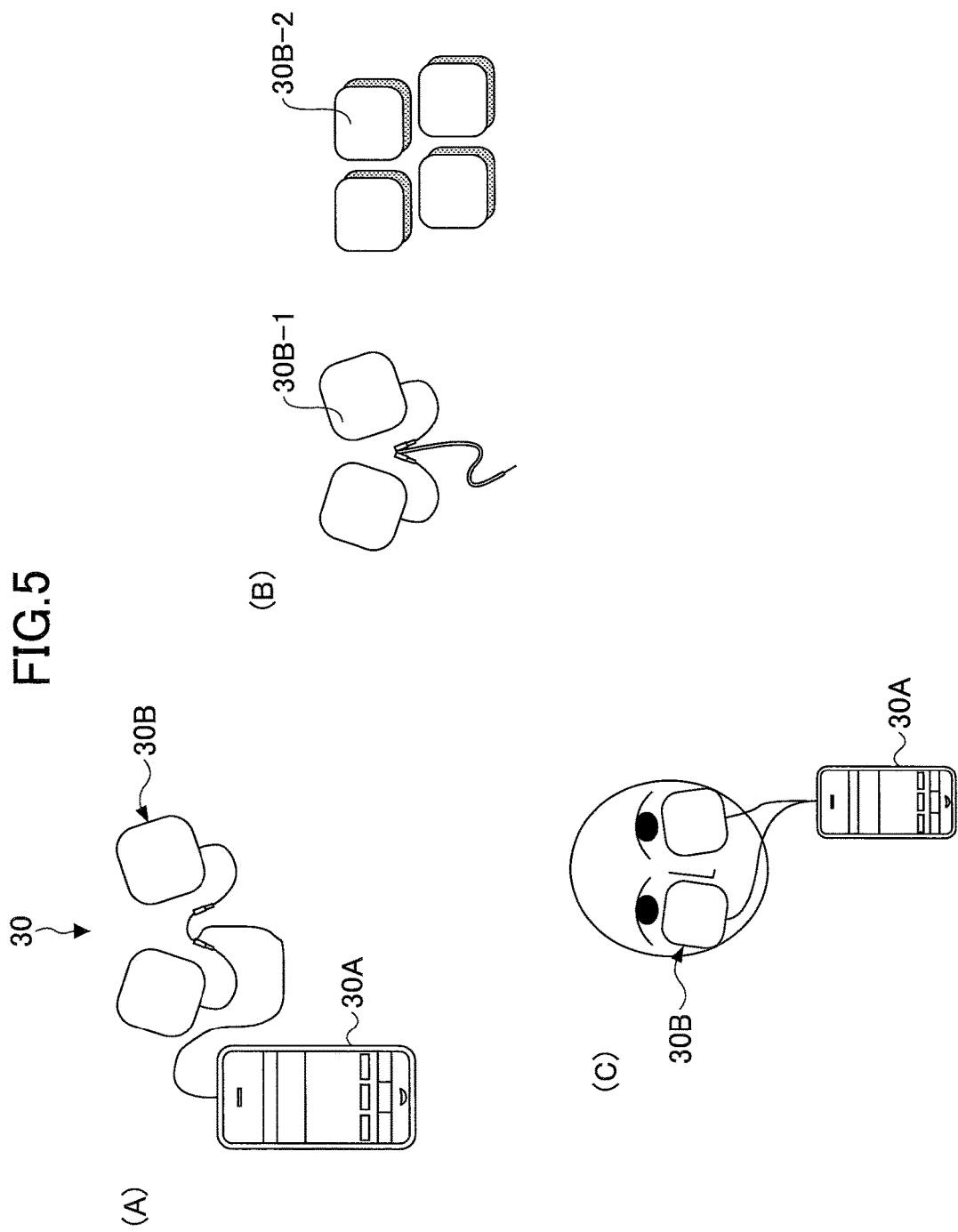
FIG. 5 is a drawing illustrating an exemplary cosmetic device connected to a content reproduction apparatus.

Next, an exemplary cosmetic device connected to the terminal apparatus 30 used as a content reproduction apparatus is described. FIG. 5 is a drawing illustrating an exemplary cosmetic device connected to a content reproduction apparatus.

In the example of FIG. 5 (A), the terminal apparatus 30 includes an apparatus body 30A and a cosmetic device 30B. The cosmetic device 30B includes electrode sheets to be directly attached to the skin of the user and an audio cable with a stereo plug to be electrically connected to the terminal apparatus 30. The stereo plug is connected to an earphone jack (or an audio terminal) of the apparatus body 30A.

When the cosmetic device 30B is configured to be connected to a dock port or a USB terminal of the apparatus body 30A, a corresponding type of plug is used.

As illustrated by FIG. 5 (B), each electrode sheet includes an electrode 30B-1 and a gel 30B-2 including a drug as a base. The gel 30B-2 is detachably attached to a surface of the electrode 30B-1 that faces the skin of the user.

For example, when an iontophoresis treatment is to be performed, the gels 30B-2 of the cosmetic device 30B including the drug are directly attached to, e.g., the cheeks of the user as illustrated by FIG. 5 (C).

When iontophoresis is performed on the user, penetration of water-soluble active ingredients, which are included in the drug in the gel 30B-2, into the skin is facilitated by charge repulsion caused by a weak electric current flowing between the electrodes 30B-1.

The gel 30B-2 including the drug may be replaced with a nonwoven fabric, a full-face mask, or a partial mask impregnated with a cosmetic liquid or a cosmetic lotion.

Also, when a low frequency therapy or the EMS where a muscle is trained by electric stimulation to reduce, for example, sagging is to be performed, a conductive gel may be attached to the electrode 30B-1.

Figure 6:
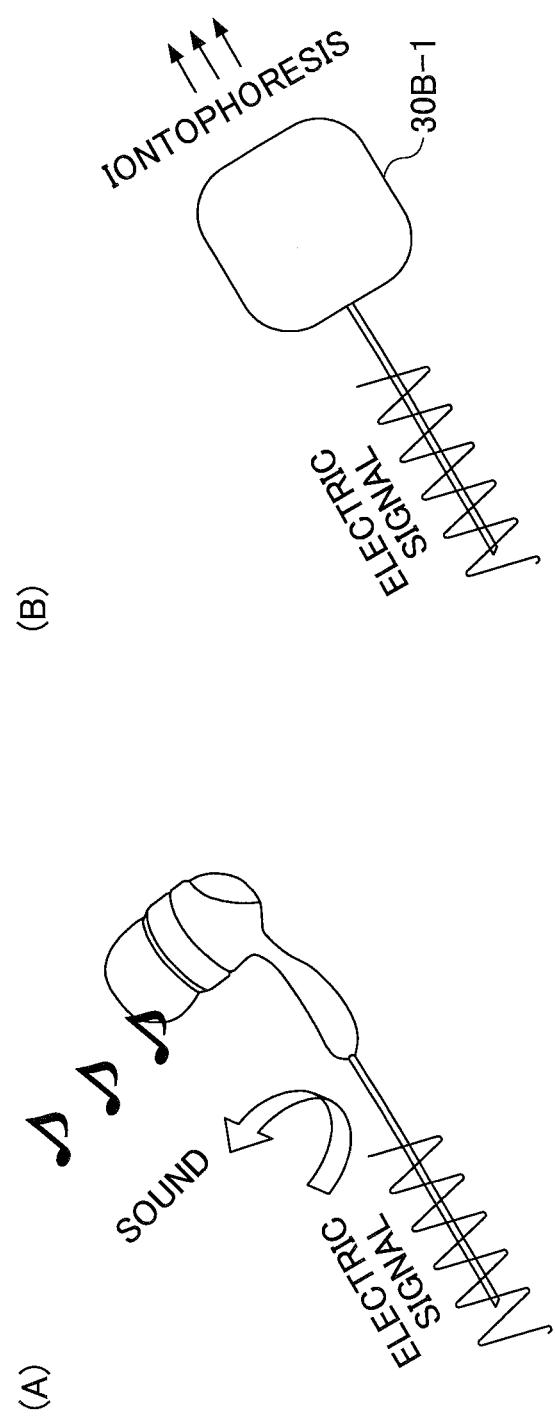
FIG. 6 is a drawing used to describe an electric signal for a cosmetic treatment.

Next, an electric signal used for a cosmetic treatment is described. FIG. 6 is a drawing used to describe an electric signal for a cosmetic treatment.

As illustrated by FIG. 6 (A), an earphone is normally connected to an audio terminal of the terminal apparatus 30 and converts an electric signal of an audio file into an audio signal. According to the present embodiment, a cosmetic treatment such as iontophoresis is performed using an electric signal input to an earphone.

More specifically, as illustrated by FIG. 6 (B), when the audio cable of the cosmetic device 30B is connected to the audio terminal of the terminal apparatus 30, an electric signal, either a Left (L) signal or a Right (R) signal of an audio file, flows through the audio cable. The electric signal is output from the electrode 30B-1 connected to an end of the audio cable. In the present embodiment, the L signal or the R signal of an audio file which corresponds to the ground (GND) potential is used as an electric signal for a cosmetic treatment such as iontophoresis.

Figure 7:
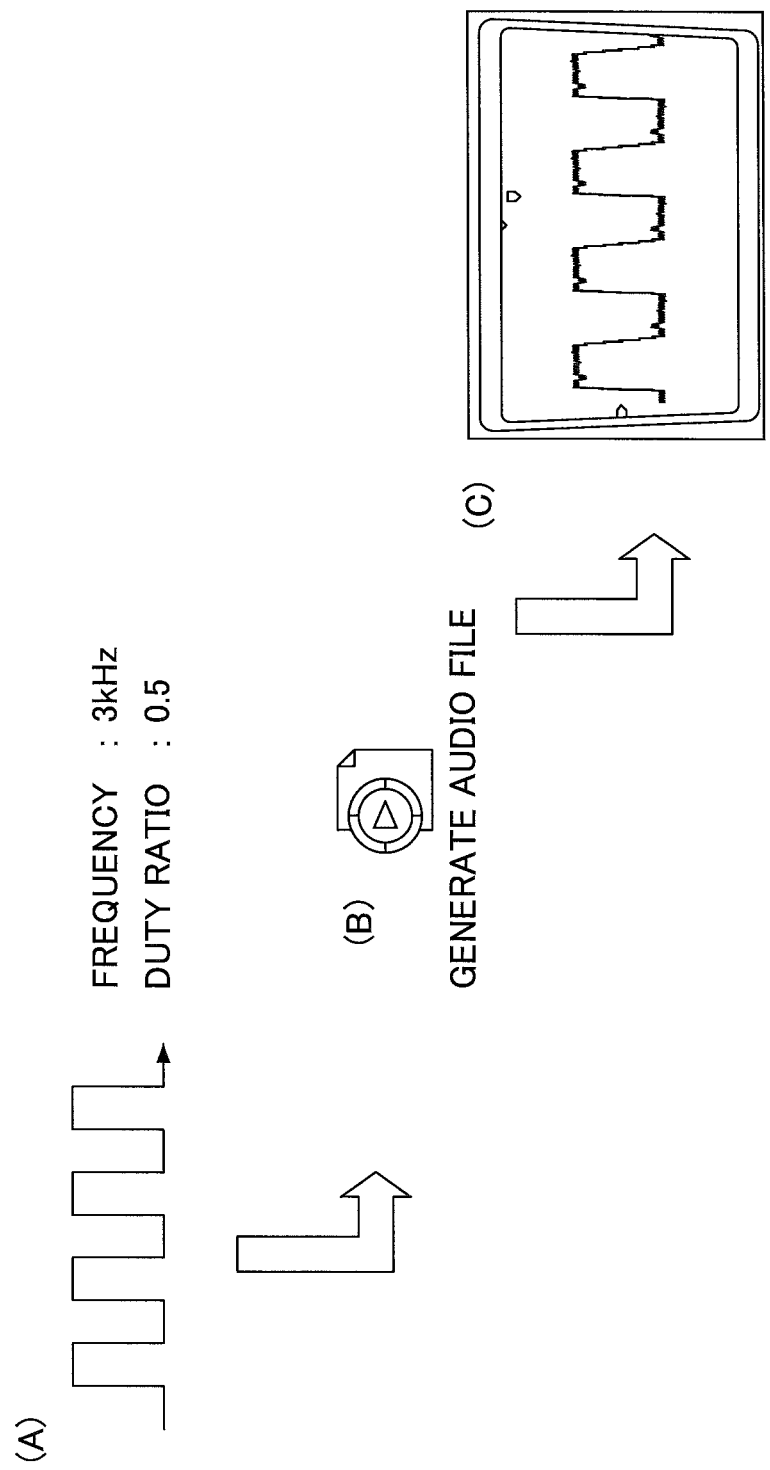
FIG. 7 is a drawing used to describe an output signal of an audio file.

Next, an audio file used to generate an electric signal for a cosmetic treatment is described. FIG. 7 is a drawing used to describe an output signal of an audio file.

As illustrated by FIG. 7 (A), the waveform normally used at, for example, a cosmetic clinic for an iontophoresis treatment is a direct-current pulse having a frequency of 3 kHz and a duty ratio of 0.5.

In the present embodiment, as illustrated by FIG. 7 (B), an audio file for generating the waveform of FIG. 7 (A) is generated.

FIG. 7 (C) illustrates an exemplary waveform of an L signal or an R signal generated based on the audio file. According to the present embodiment, the audio file is played by the terminal apparatus 30 (31, 32, 33) to output an R signal or an L signal having the waveform of FIG. 7 (C) to the electrode 30B-1 of the cosmetic device 30B.

Thus, the present embodiment makes it possible to generate and control a waveform for a cosmetic treatment using an audio file and thereby makes it possible to easily change and adjust a waveform based on the treatment to be performed, user conditions, and the polarity of a drug.

Figure 8:
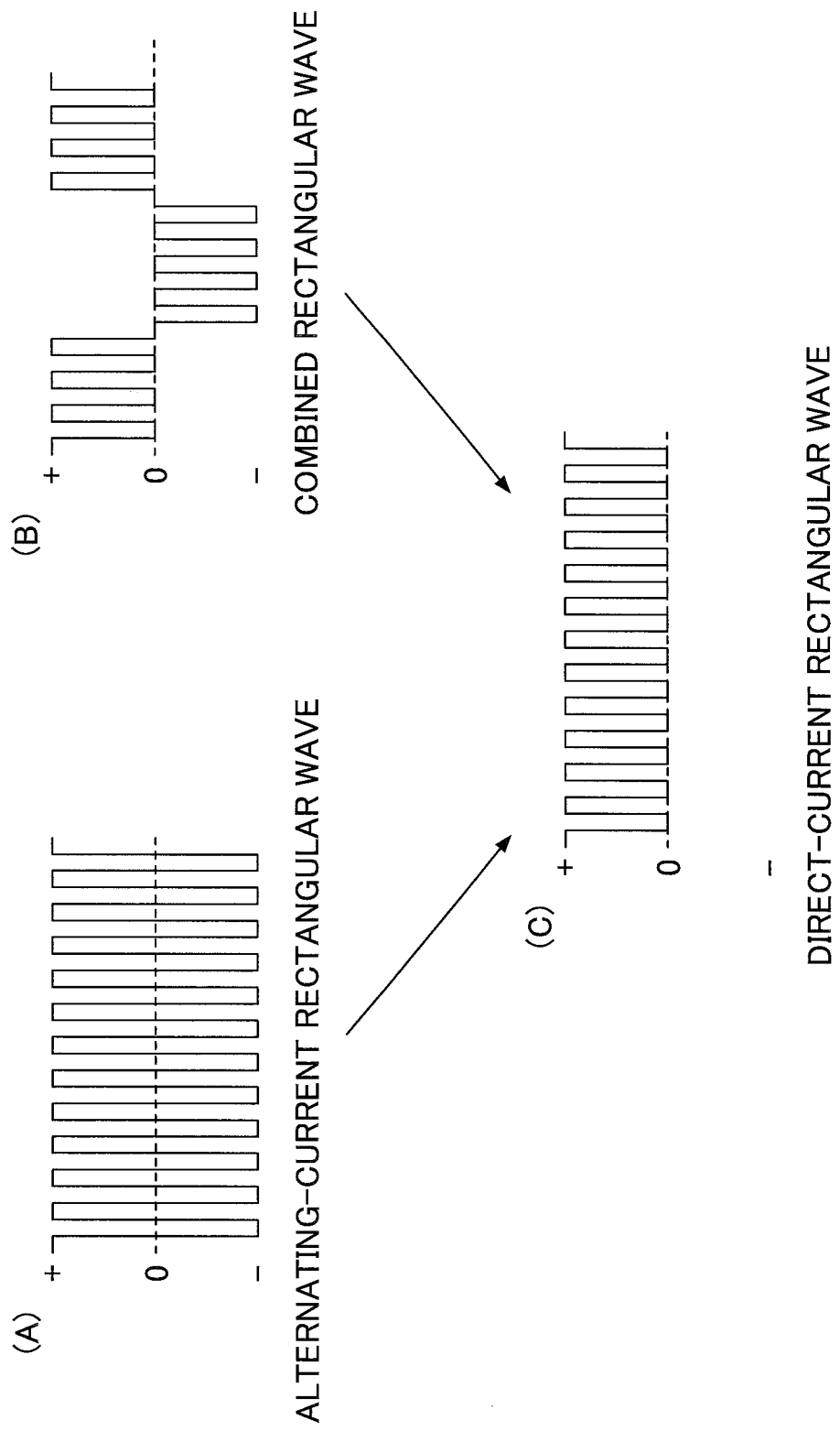
FIG. 8 is a drawing used to describe an exemplary method of generating an audio file.

Next, a method of generating an audio file for generating an L signal or an R signal having the above-described waveform is described. FIG. 8 is a drawing used to describe an exemplary method of generating an audio file. In the present embodiment, it is assumed that "YAMAHA Wave Editor TWE V2.3.1" is used to generate an audio file corresponding to a cosmetic treatment to be performed.

As described above, the waveform of the L signal or the R signal of an audio file suitable for iontophoresis is a direct-current rectangular wave with a frequency of several kHz. Meanwhile, a rectangular wave normally generated by "YAMAHA Wave Editor TWE V2.3.1" is an alternating-current rectangular wave.

Therefore, to generate a direct-current rectangular wave as described above, a rectangular wave with a predetermined frequency of, for example, 3 kHz is generated as illustrated by FIG. 8A, a rectangular wave with a low frequency of, for example, 1 Hz is generated, and the rectangular wave with a frequency of 3 kHz and the rectangular wave with a frequency of 1 Hz are combined.

Through this process, a waveform where a direct-current rectangular wave with a frequency of 3 kHz switches between the positive and negative polarities is generated as illustrated by FIG. 8 (B).

Next, a part of the direct-current rectangular wave on the positive (or negative) side is cut from the waveform of FIG. 8 (B). Then, the cut part of the direct-current rectangular wave is repeated to generate a file. The resulting file generates an output signal as illustrated by FIG. 8 (C) where a direct-current rectangular wave is repeated for a predetermined number of times.

In the present embodiment, the length of an audio file for generating a direct-current rectangular wave as illustrated by FIG. 8 (C) can be set freely to match a normal duration (e.g., from 10 to 30 min) of an iontophoresis treatment. Also, an audio file longer than a normal duration of iontophoresis may be generated and playing of the audio file may be stopped in the middle. Further, a short audio file may be generated and played repeatedly.

In the present embodiment, an audio file for generating a direct-current rectangular wave as illustrated by FIG. 8 (C) is generated as a wav file using "YAMAHA Wave Editor TWE V2.3.1". However, any other waveform editing software program such as "SOUND FORGE AUDIO STUDIO (SONY)", "SOUND IT!", or "SOUND BOOTH (registered trademark) CS4 (Adobe)" may also be used to generate the wav file.

Also, text data such as csv data or txt data may be generated according to a treatment to be performed and the text data may be converted into an audio file such as a wav file using known file conversion software.

The waveform generated by an audio file of the present embodiment is not limited to a direct-current rectangular wave. For example, the waveform of an audio file may be an alternating-current rectangular wave or a sine wave.

Figure 9:
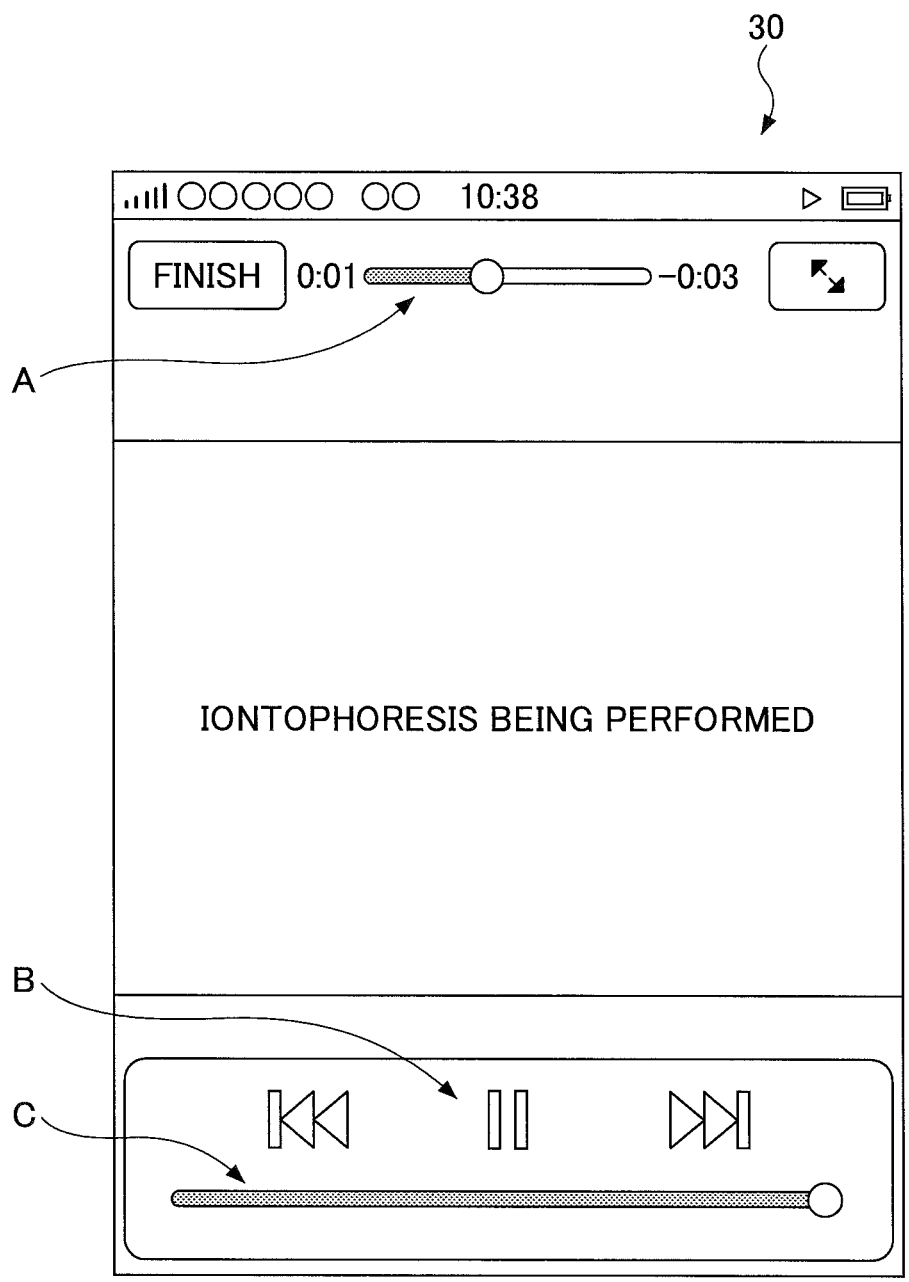
FIG. 9 is a drawing illustrating an exemplary display screen of a terminal apparatus generated by a screen generation unit.

Next, the edit-and-output unit 56 for editing and outputting an audio file for a cosmetic treatment is described. FIG. 9 is a drawing illustrating an exemplary display screen of a terminal apparatus generated by a screen generation unit.

As illustrated by FIG. 9, the screen generation unit 58 can generate a treatment display screen for a cosmetic treatment such as iontophoresis based on a music play function displayed on, for example, a music play screen.

For example, the screen generation unit 58 generates a screen displaying a function indicated by an arrow A of FIG. 9 for adjusting the number of repetitions and the length of an audio file, a function indicated by an arrow B of FIG. 9 for playing and stopping an audio file, and a function indicated by an arrow C of FIG. 9 for adjusting the output strength of an audio file.

When, for example, the user changes the number of repetitions or the length of an audio file using the screen of FIG. 9, the edit-and-output unit 56 adjusts the number of repetitions or the length of the audio file being played and outputs or plays the changed audio file. Also, the edit-and-output unit 56 plays and stops an audio file in response to user instructions to play and stop the audio file. Thus, the edit-and-output unit 56 makes it possible to change the duration for which an audio file is played.

Further, when the user adjusts or changes the output strength of an audio file, the edit-and-output unit 56 adjusts the output strength (or the signal strength) of the audio file being played and outputs or plays the audio file.

In the present embodiment, editing an audio file includes adjustments of the amplitude, frequency, and polarity of a current waveform. To adjust the amplitude or frequency of a waveform, an existing audio reproduction function may be used. For example, the output strength of an audio file may be adjusted by changing the amplitude of the waveform in a manner similar to adjusting the sound volume, and the play speed of an audio file may be adjusted by controlling the frequency in a manner similar to adjusting the sound pitch. However, the present invention is not limited to these examples, and various control functions dedicated to respective purposes may be provided.

Also, audio files having positive and negative polarities may be stored in the storage unit 52 and the polarity of a waveform may be changed by selecting one of the audio files corresponding to the polarity of a drug to be introduced.

The screen of FIG. 9 may include various control functions, for example, to change a waveform to match the polarity of a drug, to change the number of audio files to be played, to change the order in which audio files are played, to change treatments to be performed, and to change a combination of audio files with different purposes.

As described above, the edit-and-output unit 56 of the present embodiment makes it possible to control an audio file and thereby makes it possible to easily adjust and control a treatment to be performed.

Figure 10:
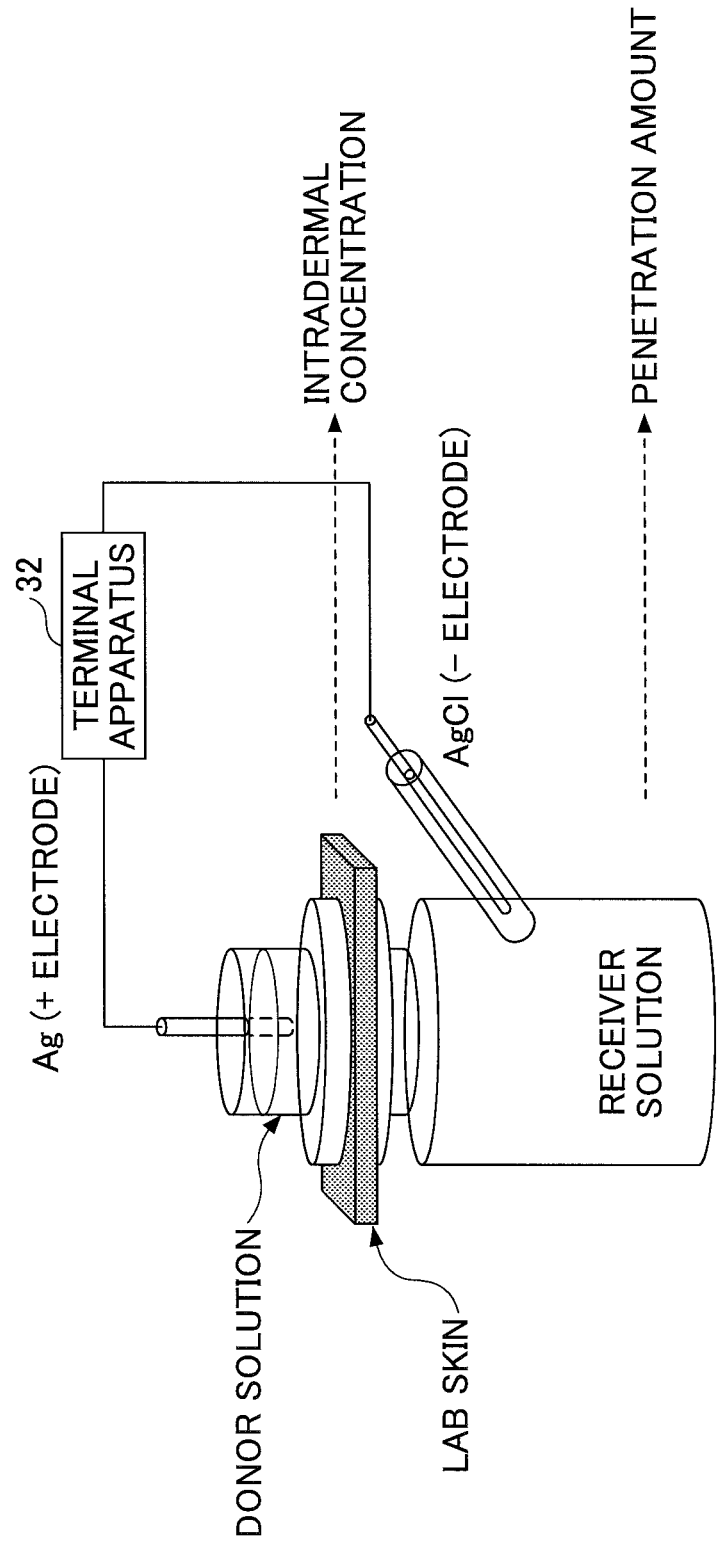
FIG. 10 is a drawing used to describe an in-vitro iontophoresis experiment.
Figure 11A:
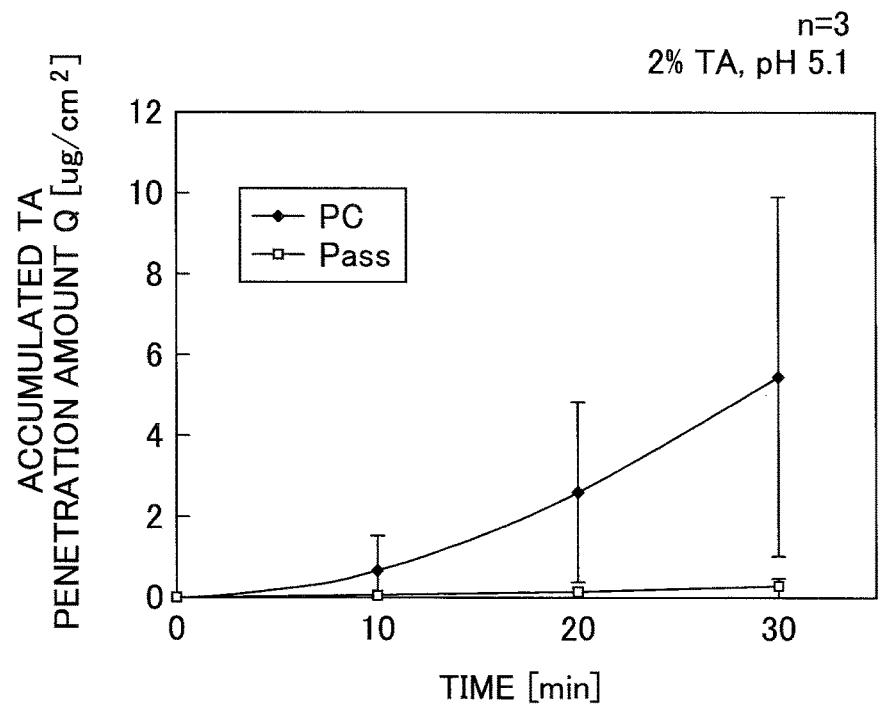
FIG. 11A is a graph illustrating the accumulated amount of penetration of cationized tranexamic acid (TA)
Figure 11B:
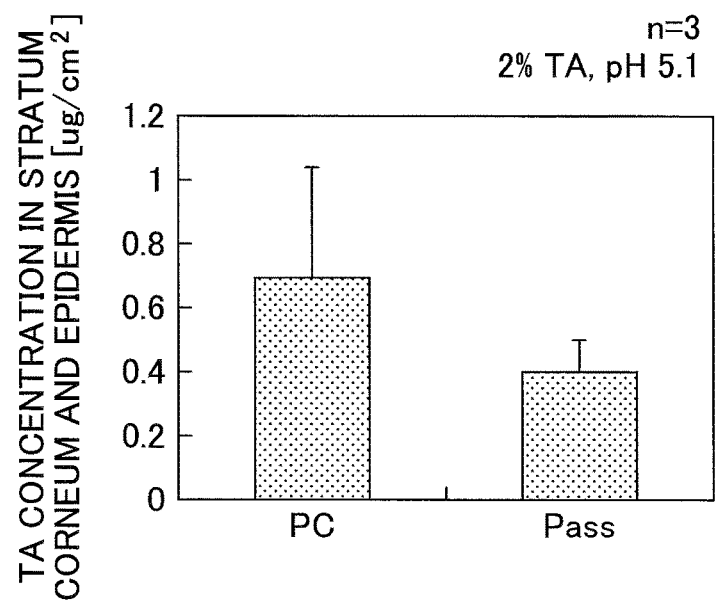
FIG. 11B is a graph illustrating the concentration of cationized tranexamic acid (TA) in stratum corneum and epidermis.
Figure 11C:
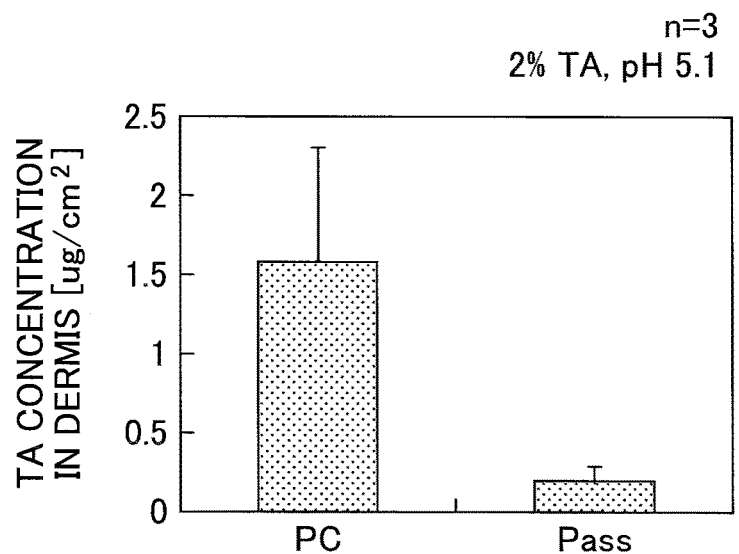
FIG. 11C is a graph illustrating the concentration of cationized tranexamic acid (TA) in dermis.

An experiment of iontophoresis performed at a constant voltage using a content reproduction apparatus of the present embodiment and the results of the experiment are described below. FIG. 10 is a drawing used to describe an in-vitro iontophoresis experiment. FIGS. 11A, 11B, and 11C illustrate the accumulated amount of penetration of cationized tranexamic acid (TA), the concentration of cationized TA in stratum corneum and epidermis, and the concentration of cationized TA in dermis.

In the experiment, Franz cells were used as an iontophoresis experiment device; the terminal apparatus 32 (e.g., a PC), which is an example of a content reproduction apparatus of the present embodiment, was used as a power supply; and the Windows (registered trademark) Media Player was used as a content reproduction application. Also, a storage medium storing a content reproduction program outputting a constant voltage of 1.8 V was used.

Further, an Ag electrode was used as a positive electrode, an AgCl electrode was used as a negative electrode, a tranexamic acid solution was used as a donor solution, and phosphate buffered saline (pH 7.4) was used as a receiver solution.

As illustrated in FIG. 10, a lab skin (commercially-available excised skin of hairless mouse) was placed between cells preheated to 37 degrees, 7.5 ml of the receiver solution was added to the cell on the dermal layer side, and 1 ml of the donor solution was added to the cell on the stratum corneum side. The positive electrode was used as the introduction electrode. The Ag electrode was placed at the donor solution side, the AgCl electrode was placed at the receiver solution side, and the content reproduction program read from the storage medium was executed for 30 minutes to apply a constant voltage of 1.8 V. Also, a comparative experiment was performed without applying an electric current (i.e., normal application of the drug which is indicated by "Pass").

In the experiments, the concentration of tranexamic acid in the receiver solution was measured by microdetermination using liquid chromatography-mass spectrometry (LC-MS) to obtain the accumulated amount of penetration. Here, the accumulated amount of penetration indicates the amount of a drug penetrated per unit area of skin ($\mu g/cm^2$).

Also in the experiments, the concentration of tranexamic acid in stratum corneum and epidermis and the concentration of tranexamic acid in dermis were measured using the hairless mouse skin placed between the cells.

FIG. 11A illustrates the accumulated amount of penetration of tranexamic acid in relation to the passage of time. FIGS. 11B and 11C illustrate intradermal concentrations of tranexamic acid (the concentration in stratum corneum and epidermis and the concentration in dermis [$\mu g/cm^2$]).

Each of the values in FIGS. 11A, 11B, and 11C indicates an average value±SD (n=3) of the intradermal concentration when a tranexamic acid (TA) solution (2%, pH 5.1) is introduced from the positive electrode. Also in FIGS. 11A, 11B, and 11C, "PC" indicates the experiment where iontophoresis was performed on the skin using a PC as a content reproduction apparatus and "Pass" indicates the comparative experiment where no electric current was applied to the skin.

As illustrated in FIG. 11A, the accumulated amount of penetration of tranexamic acid in the iontophoresis experiment "PC" becomes greater than the accumulated amount of penetration of tranexamic acid in the experiment "Pass" as time passes.

As illustrated in FIG. 11B, the concentration of tranexamic acid in stratum corneum and epidermis in the iontophoresis experiment "PC" is greater than the concentration of tranexamic acid in stratum corneum and epidermis in the experiment "Pass". Also, as illustrated in FIG. 11C, the concentration of tranexamic acid in dermis in the iontophoresis experiment "PC" is greater than the concentration of tranexamic acid in dermis in the experiment "Pass".

Figure 12A:
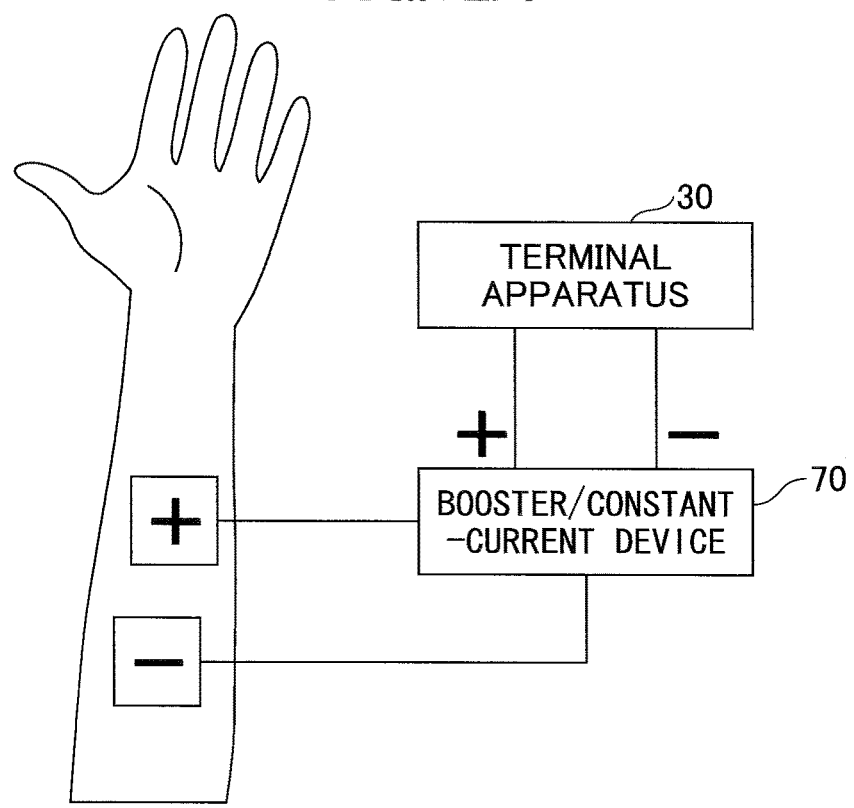
FIG. 12A is a drawing used to describe an iontophoresis experiment using a booster/constant-current device.
Figure 12B:
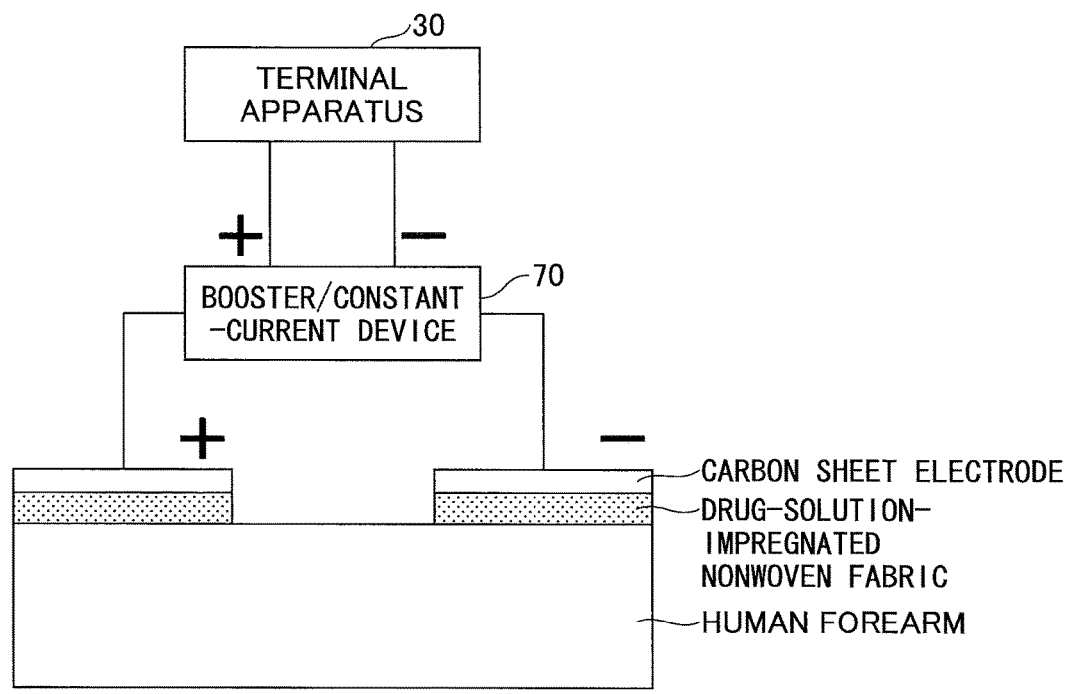
FIG. 12B is a drawing used to describe an iontophoresis experiment using a booster/constant-current device.

Next, an iontophoresis treatment performed using a booster/constant-current device together with a content reproduction apparatus of the present embodiment is described with reference to FIGS. 12A through 15. FIGS. 12A and 12B are drawings used to describe an iontophoresis experiment using a booster/constant-current device. FIG. 12A illustrates an experiment where iontophoresis is performed on a forearm of a human (human forearm), and FIG. 12B illustrates the relationship among carbon sheet electrodes, drug-solution-impregnated nonwoven fabrics, and a human forearm in the experiment of FIG. 12A.

As illustrated by FIGS. 12A and 12B, the terminal apparatus 30 used as a content reproduction apparatus outputs an L signal or an R signal, and the output signal is input via, for example, an audio cable to a booster/constant-current device 70. A signal output from the booster/constant-current device 70 is output via, for example, an audio cable to the carbon sheet electrode (positive) and the carbon sheet electrode (negative). The booster/constant-current device 70 is described later.

The human forearm was washed once using soap and left at rest for one minute. Then, nonwoven fabrics impregnated with a drug solution (drug-solution-impregnated nonwoven fabrics) were placed on the forearm, and the carbon sheet electrode (positive) and the carbon sheet electrode (negative) were placed on the drug-solution-impregnated nonwoven fabrics. The drug solution was prepared by adding about 2% of tranexamic acid (TA) and adjusting the pH to 5.0.

An alternative-current rectangular wave with a frequency of 3 kHz was output from the terminal apparatus 30, and a constant current of 250 µA was output for about 15 minutes from the booster/constant-current device 70. Then, the forearm was washed once using soap and a sample of stratum corneum was obtained. Also, in a comparative experiment (indicated by "Pass"), the drug-solution-impregnated nonwoven fabrics were placed on the forearm without applying the constant current and a sample of stratum corneum was obtained.

Figure 13:
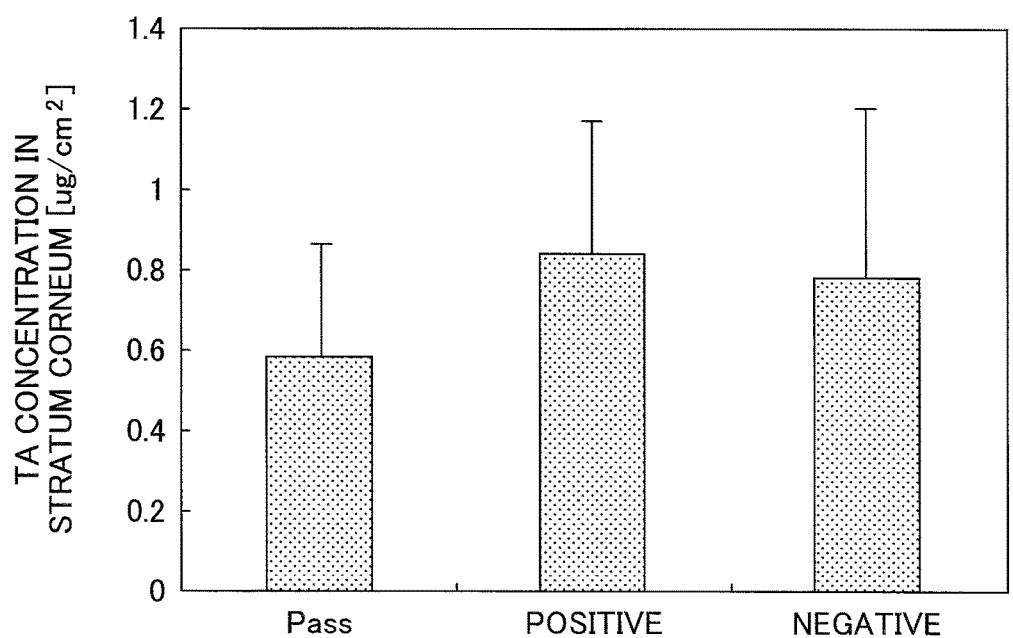
FIG. 13 is a graph illustrating the concentration of tranexamic acid (TA) in stratum corneum.

FIG. 13 is a graph illustrating the concentration of tranexamic acid (TA) in stratum corneum. In FIG. 13, "Pass" indicates a sample of stratum corneum obtained in the comparative experiment "Pass" where no electric current was applied, "Positive" indicates a sample of stratum corneum obtained from a skin where a positive electric current was applied, and "Negative" indicates a sample of stratum corneum obtained from a skin where a negative electric current was applied. Also in FIG. 13, the vertical axis indicates the concentration ($\mu g/cm^2$) of tranexamic acid (TA) in stratum corneum.

As illustrated in FIG. 13, the concentrations of tranexamic acid in the samples of stratum corneum indicated by "Positive" and "Negative" are greater than the concentration of tranexamic acid in the sample of stratum corneum indicated by "Pass".

Figure 14:
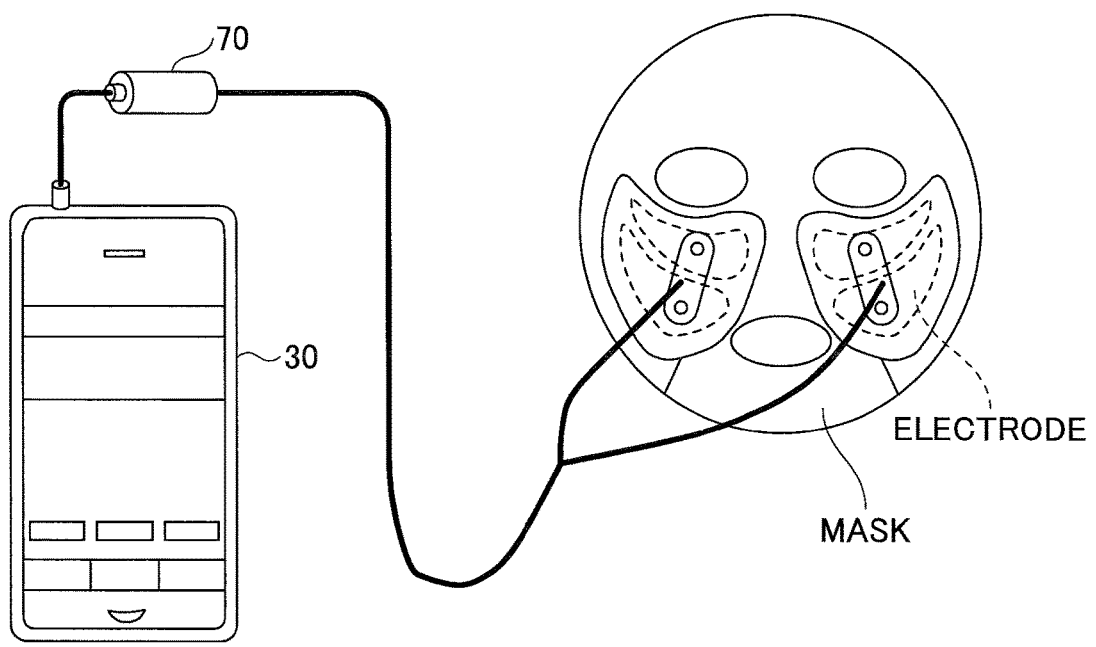
FIG. 14 is a drawing used to describe an iontophoresis treatment performed using a booster/constant-current device.

FIG. 14 is a drawing used to describe an iontophoresis treatment performed using a booster/constant-current device. As illustrated in FIG. 14, when performing iontophoresis on a human face, a negative electrode and a positive electrode are attached to a mask impregnated with, for example, a cosmetic lotion.

The electrodes attached to the mask are connected via the booster/constant-current device 70 to the terminal apparatus 30. This configuration makes it possible to perform iontophoresis using a content reproduction apparatus equipped with the booster/constant-current device 70.

Figure 15:
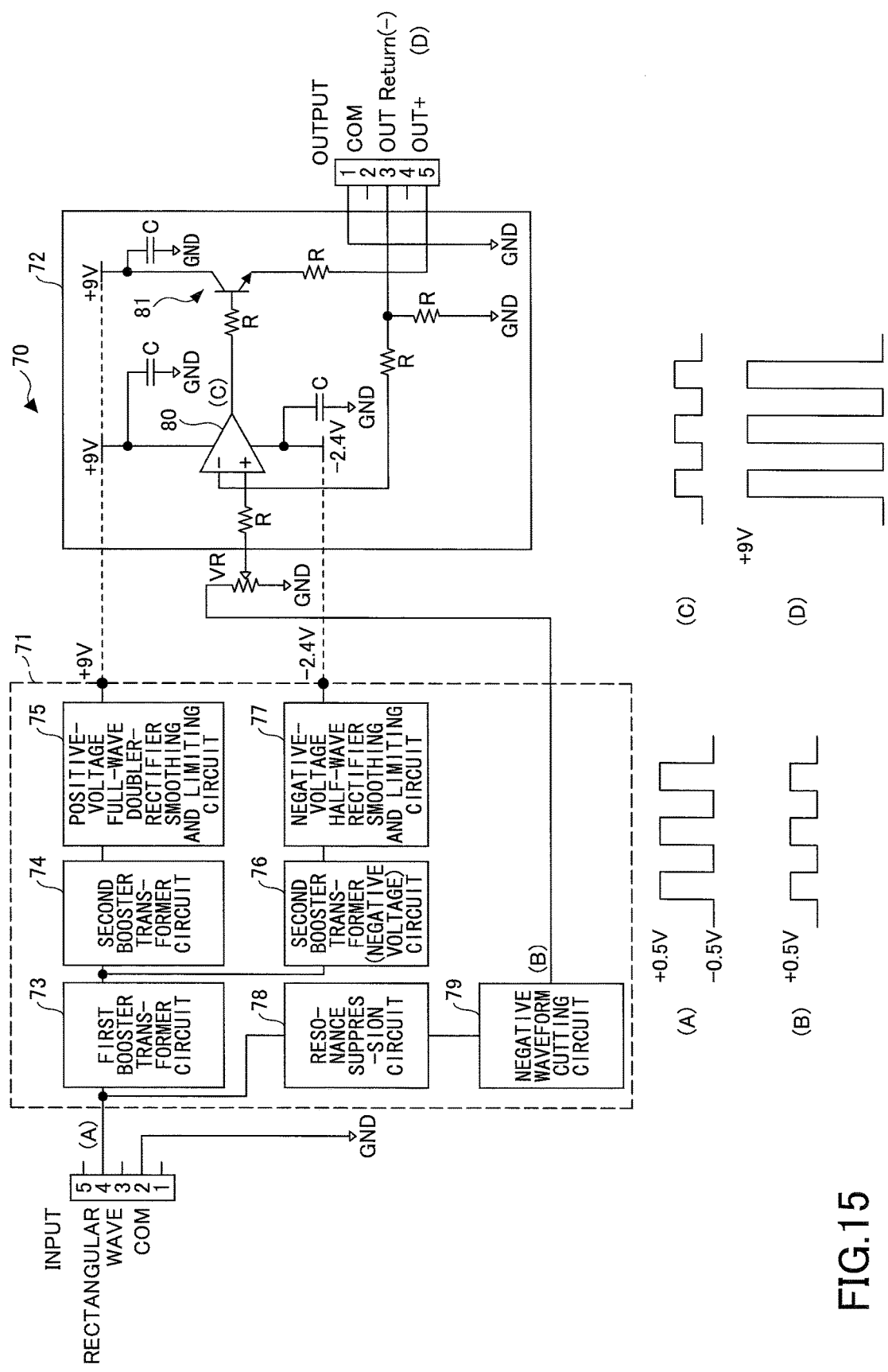
FIG. 15 is a drawing illustrating an exemplary configuration of a booster/constant-current device that increases the voltage of an waveform signal output from a terminal apparatus and keeps the current of the waveform signal constant.

FIG. 15 is a drawing illustrating an exemplary configuration of a booster/constant-current device that increases the voltage of a waveform signal output from a terminal apparatus and keeps the current of the waveform signal constant. As illustrated in FIG. 15, the booster/constant-current device 70 includes a booster circuit 71 and a constant current circuit 72.

The booster circuit 71 includes a first booster transformer circuit 73, a second booster transformer circuit 74, a positive-voltage full-wave doubler-rectifier smoothing and limiting circuit 75, a second booster transformer (negative voltage) circuit 76, a negative-voltage half-wave rectifier smoothing and limiting circuit 77, a resonance suppression circuit 78, and a negative waveform cutting circuit 79.

The booster circuit 71 receives a signal waveform (e.g., an alternating-current rectangular wave of ±0.5 V) illustrated by FIG. 15 (A) via a fourth input pin. The signal waveform of FIG. 15 (A) is input to the first booster transformer circuit 73 and the resonance suppression circuit 78.

The first booster transformer circuit 73 increases the voltage of the input signal waveform to, for example, 1.5 V. The second booster transformer circuit 74 increases the voltage of the signal waveform output from the first booster transformer circuit 73 to, for example, 4.5 V.

The positive-voltage full-wave doubler-rectifier smoothing and limiting circuit 75 performs full-wave rectification on the positive voltage of the signal waveform output from the second booster transformer circuit 74 to double the positive voltage (e.g., to 9.0 V), rectifies the doubled voltage, smoothes the rectified voltage, and limits the smoothed voltage to, for example, 9 V.

The second booster transformer (negative voltage) circuit 76 increases the voltage of the signal waveform output from the first booster transformer circuit 74 to, for example, 2.5 V.

The negative-voltage half-wave rectifier smoothing and limiting circuit 77 performs half-wave rectification on the negative voltage of the signal waveform output from the second booster transformer (negative voltage) circuit 76, smoothes the rectified voltage, and limits the smoothed voltage to, for example, −2.4 V.

The resonance suppression circuit 78 suppresses the resonance of the input signal waveform. The negative waveform cutting circuit 79 extracts a signal for controlling an output current waveform from a signal waveform output from the resonance suppression circuit 78 and thereby cuts the negative waveform from the signal waveform. For example, the negative waveform cutting circuit 79 outputs a signal waveform (e.g., a signal waveform of +0.5 V) illustrated by FIG. 15 (B).

The constant current circuit 72 includes an operational amplifier 80 and a transistor 81. The signal waveform output from the negative waveform cutting circuit 79 of the booster circuit 71 is input to the constant current circuit 72 via a setting circuit that sets an output current similar to a positive input waveform. The signal waveform input to the constant current circuit 72 is input to a non-inverting input terminal of the operational amplifier 80. Meanwhile, a return signal from a third output pin is input to an inverting input terminal of the operational amplifier 80.

The operational amplifier 80, for example, outputs a signal waveform as illustrated by FIG. 15 (C). The signal waveform output from the operational amplifier 80 is input to the base of the transistor 81 and output via a resistor provided at the emitter side of the transistor 81 to a fifth output pin. For example, the fifth output pin outputs a signal waveform (e.g., a signal waveform of +9 V) as illustrated by FIG. 15 (D).

As described above, the booster/constant-current device 70 increases the voltage of an input waveform (waveform of an audio file) and keeps the current of the input waveform constant. Thus, the booster/constant-current device 70 makes it possible to improve the effect of iontophoresis by increasing the voltage and improve the safety of iontophoresis on skin by keeping the output current constant.

Figure 16A:
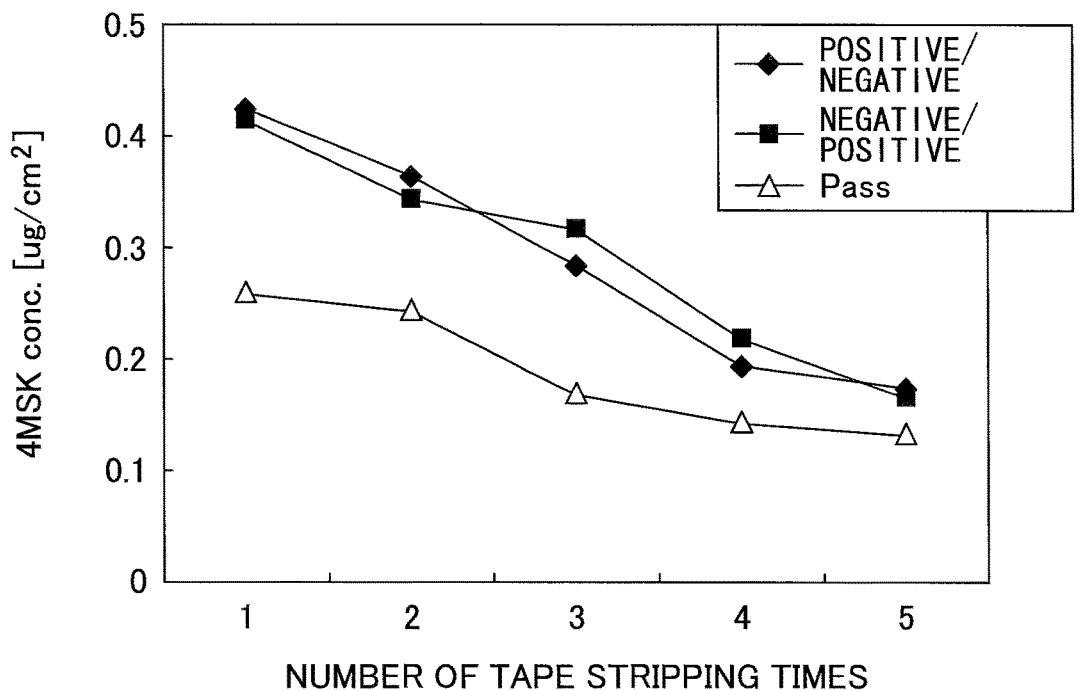
FIG. 16A is a graph illustrating results of iontophoresis performed using a cosmetic device connected to an earphone jack.
Figure 16B:
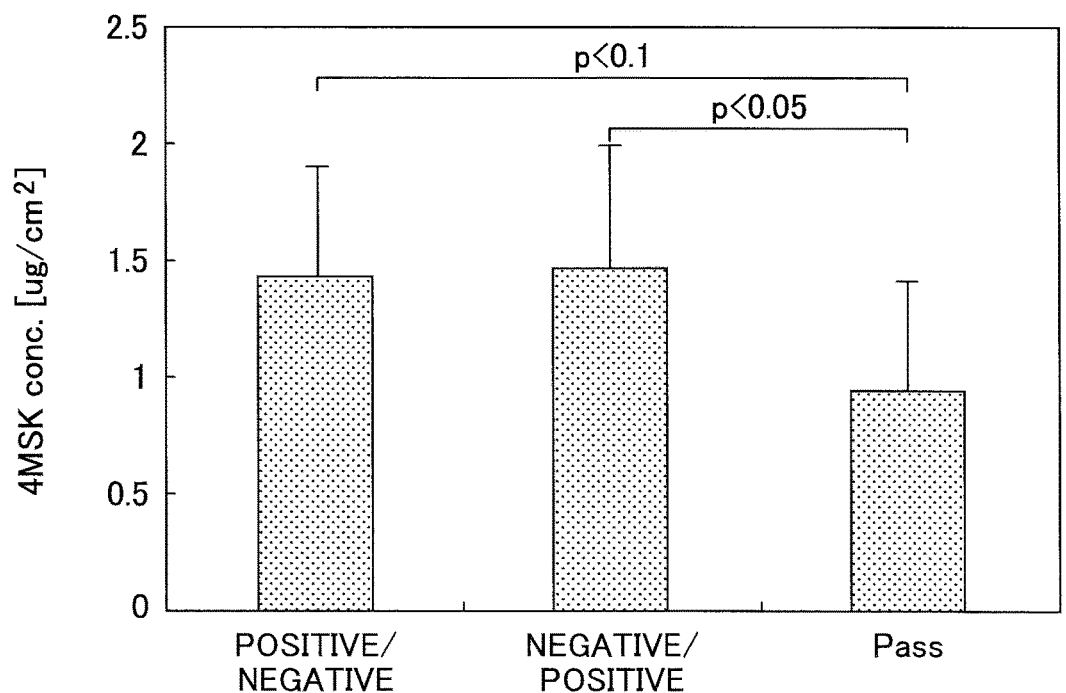
FIG. 16B is a graph illustrating results of iontophoresis performed using a cosmetic device connected to an earphone jack.

Next, results of an iontophoresis experiment performed using the terminal apparatus 30 as a content reproduction apparatus and the cosmetic device 30B-1 of FIG. 6 connected to the earphone jack of the terminal apparatus 30 are described. FIGS. 16A and 16B are graphs illustrating results of iontophoresis performed using a cosmetic device connected to an earphone jack.

In the iontophoresis experiment, a carbon sheet electrode was used as the electrode 30B-1 illustrated in FIG. 6. The electrode 30B-1 was connected via an audio cable to the earphone jack. The electrode 30B-1 was placed on a human face (e.g., cheek skin) via a nonwoven fabric impregnated with a drug solution. The drug solution was prepared by adding about 1% of 4-methoxy salicylic acid KCl (4MSK) that becomes negative ions and adjusting the pH to 6.0.

An alternating current with a frequency of 1 Hz was output and a voltage of about ±1.9 V was applied for about 10 minutes by the terminal apparatus 30. Then, the face was washed once using soap and a sample of stratum corneum was obtained. Also, in a comparison experiment (indicated by "Pass"), the drug-solution-impregnated nonwoven fabric was placed on the human face without applying an electric current, and a sample of stratum corneum was obtained.

FIG. 16A illustrates the relationship between the number of tape stripping times of a skin on which iontophoresis was performed as described above and the concentration of the drug solution. In FIG. 16A, the horizontal axis indicates the number of tape stripping times and the vertical axis indicates the concentration ($\mu g/cm^2$) of 4MSK. Here, the number of tape stripping times indicates the depth of skin from the skin surface, and the conditions of skin at different depths can be obtained by changing the number of tape stripping times.

Also in FIG. 16A, "positive/negative" indicates the concentration in a sample of stratum corneum where an alternating current starting from the positive pole was applied to the electrode, "negative/positive" indicates the concentration in a sample of stratum corneum where an alternating current starting from the negative pole was applied to the electrode, and "Pass" indicates the concentration in a sample of stratum corneum where no electric current was applied.

As illustrated in FIG. 16A, the concentrations in the samples of stratum corneum where "positive/negative" and "negative/positive" alternating currents were applied are greater than the concentration in the sample of stratum corneum indicated by "Pass", and the difference is greater near the skin surface, i.e., when the number of tape stripping times is 1 through 3.

FIG. 16B is a graph illustrating the concentration of 4MSK in stratum corneum. In FIG. 16B, "positive/negative" indicates the concentration in a skin where the "positive/ negative" alternating current was applied, "negative/positive" indicates the concentration in a skin where the "negative/positive" alternating current was applied, and "Pass" indicates the concentration in a skin where no electric current was applied. Also in FIG. 16B, the vertical axis indicates the concentration ($\mu g/cm^2$) of 4MSK in stratum corneum.

As illustrated in FIG. 16B, the concentrations of 4MSK in the skins where the "positive/negative" alternating current and the "negative/positive" alternating current were applied are greater than the concentration of 4MSK in the skin indicated by "Pass".

Figure 17A:
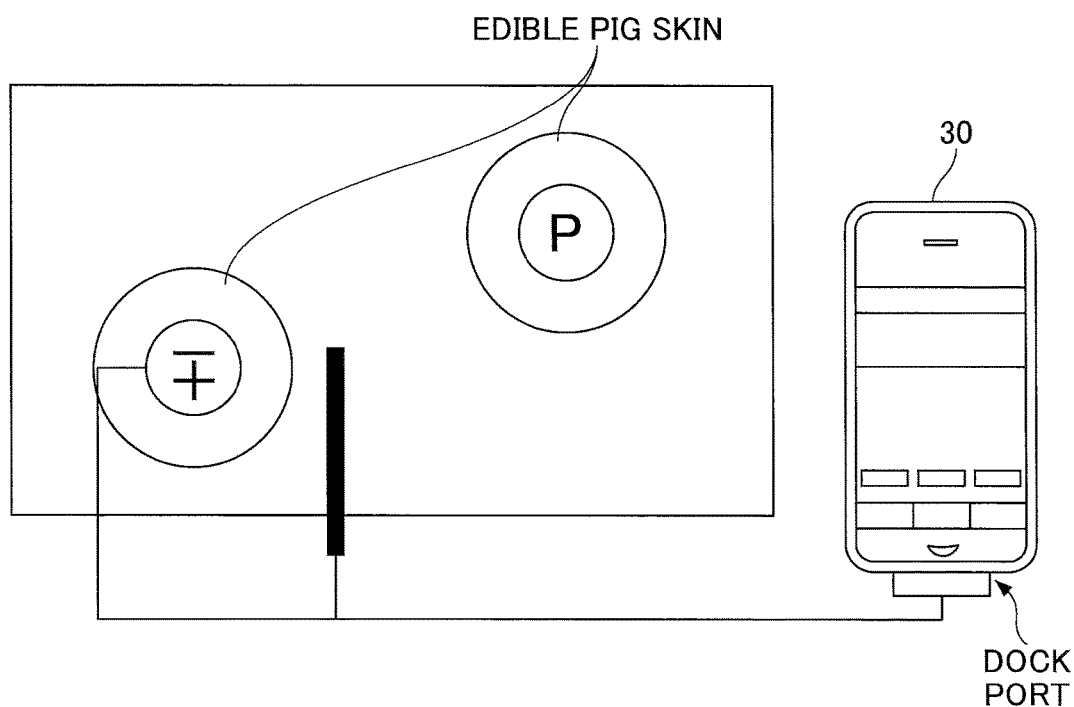
FIG. 17A is a drawing illustrating an example where a dock port is used.
Figure 17B:
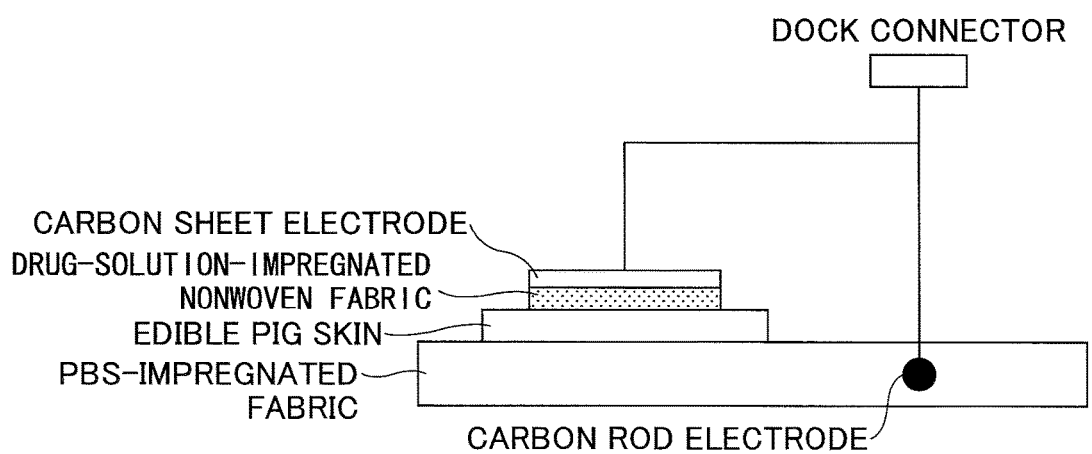
FIG. 17B is a drawing illustrating an example where a dock port is used.
Figure 17C:
FIG. 17C is a drawing illustrating an example where a dock port is used.

Next, an example where a content reproduction apparatus includes a dock port is described. FIGS. 17A, 17B, and 17C are drawings illustrating an example where a dock port is used. FIG. 17A illustrates an iontophoresis experiment performed using a dock port of a content reproduction apparatus. FIG. 17B illustrates the positional relationship among a carbon sheet electrode, a drug-solution-impregnated nonwoven fabric, an edible pig skin, a PBS-impregnated fabric, and a carbon rod electrode. FIG. 17C illustrates exemplary results of the experiment illustrated by FIG. 17A.

As illustrated by FIGS. 17A and 17B, an edible pig skin washed once with water was placed on a fabric (PBS-impregnated fabric) impregnated with phosphate buffered saline (PBS). Two sets of the edible pig skin and the drug-solution-impregnated nonwoven fabric were provided in FIG. 17A. A carbon sheet electrode was placed on the drug-solution-impregnated nonwoven fabric of one of the sets, and no carbon sheet electrode was placed on the drug-solution-impregnated nonwoven fabric of the other one of the sets (indicated by "P"). Also, a carbon rod electrode was placed in the PBS-impregnated fabric as a counter electrode for the carbon sheet electrode.

The carbon sheet electrode and the carbon rod electrode of FIG. 17A are connected via a dock connector illustrated in FIG. 17B to the dock port of the terminal apparatus 30. The L signal or the R signal was supplied to the carbon sheet electrode and the GND potential was supplied to the carbon rod electrode. Alternatively, a signal with a phase opposite to the phase of the L signal or the R signal supplied to the carbon sheet electrode may be supplied to the carbon rod electrode. The drug solution was prepared by adding about 0.1% of fluorescein Na and adjusting the pH to 6.0.

An alternating current with a frequency of 1 Hz was output and a voltage of about ±1.9 V was applied for about 10 minutes by the terminal apparatus 30. Then, the edible pig skins were washed once and an image of the appearance of the edible pig skins was taken by illuminating the edible pig skins with a UV lamp.

As illustrated in FIG. 17C, the local penetration of the drug solution into the skin where an alternating current was applied from the negative electrode illustrated in FIG. 17A is greater than the penetration of the drug solution into the skin where no alternating current was applied ("Pass").

Next, a method for playing music while performing iontophoresis using a content reproduction apparatus of the present embodiment is described. FIG. 18 is a drawing used to describe a method for playing music while performing an iontophoresis treatment. According to the present embodiment, iontophoresis is performed using an apparatus capable of playing music. Therefore, it is possible to play music while performing iontophoresis.

For example, earphones (speakers) with electrodes as illustrated by FIG. 18 (A) may be used for this purpose. In this method, a waveform for iontophoresis (IP waveform) as illustrated by FIG. 18 (B) is combined with a waveform of music as illustrated by FIG. 18 (C) to generate a combined waveform as illustrated by FIG. 18 (D). As a result, a waveform as illustrated by FIG. 18 (E) can be output.

The frequency of the waveform for iontophoresis illustrated by FIG. 18 (B) is preferably about 1 Hz that is below the audible frequency range of a human.

By using a waveform as illustrated by FIG. 18 (E), the user can perform iontophoresis while listening to music with earphones.

Sound synthesis can be performed using a known sound synthesis method (or application) and therefore the details of sound synthesis are omitted here. For example, the ratio of the amplitude of the iontophoresis waveform of FIG. 18 (B) to the amplitude of the music waveform of FIG. 18 (C) in a combined waveform may be adjusted to optimize the balance between the intensity of iontophoresis and the volume of music.

Music to be combined with an iontophoresis waveform may be selected freely by the user. Also, pieces of music may be registered beforehand and one of the pieces of music may be selected based on the iontophoresis waveform, the treatment to be performed, and the treatment duration. Further, instead of music, a waveform of voice guidance about the details of a treatment may be combined with an iontophoresis waveform.

As described above, the present embodiment makes it possible to easily perform a cosmetic treatment with a widely-used content reproduction apparatus. Also, the present embodiment makes it possible to perform a cosmetic treatment at a low cost by using a music reproduction function of a widely-used content reproduction apparatus. Also with the present embodiment, it is possible to use an audio file to control an output signal for a cosmetic treatment. This in turn makes it possible to easily change or adjust the waveform of the output signal depending on a treatment to be performed and user conditions.

Content files used in the present embodiment may be provided for respective cosmetic treatments and users, and a user can select one of the content files based, for example, on a treatment to be performed, skin resistance obtained by diagnosis of the user, and/or the polarity of a drug. When a terminal apparatus connectable to the Internet is used, content files can be downloaded from an Internet site. Meanwhile, when a terminal apparatus (e.g., iPod or a game machine) not connectable to the Internet is used, content files may be downloaded to a PC connectable to the Internet and obtained from the PC via a cable connection or via a storage medium such as a CD, a DVD, a USB memory, or an SD card.

The content reproduction program described above may be provided as an application. Such an application may include functions such as a downloading function for downloading content data, a reproduction function for playing the downloaded content data, a selection function for selecting a cosmetic treatment, a counseling function for performing counseling on a cosmetic treatment, a measuring function for measuring the skin condition of a user, and an image display function for displaying, for example, a usage guide, precautions, and drug efficacy. The application may be used on an apparatus (e.g., a PC or a smartphone) that allows installation of applications. For an apparatus (e.g., a music player such as iPod) that does not allow installation of applications, the content reproduction program may be preinstalled.

A content reproduction apparatus of the present embodiment may also be used for purposes other than cosmetic treatments. For example, a content reproduction apparatus of the present embodiment may be used as a hot-and-cold therapy device, a light emitting diode (LED) therapy device, a vibrator, or a skin diagnosis device. Also, a content reproduction apparatus of the present embodiment may include a dedicated plug for connecting, for example, a cosmetic device.

Although the preferred embodiments of the present invention are described above, the present invention is not limited to the specifically disclosed embodiments, and variations and modifications may be made without departing from the scope of the present invention.

The present international application is based on and claims the benefit of priority of Japanese Patent Application No. 2010-251337 filed on Nov. 9, 2010, and Japanese Patent Application No. 2011-241721 filed on Nov. 2, 2011, the entire contents of which are hereby incorporated herein by reference.

The invention claimed is:

1. A content reproduction apparatus comprising:
a storage that stores a plurality of content files;
a memory that stores a program; and
a processor that executes the program stored in the memory to perform a process including
setting a treatment based on a treatment condition input by a user;
obtaining, from the storage, a content file that corresponds to the set treatment;
determining whether the content file includes an audio file;
when it is determined that the content file includes no audio file, converting the content file into the audio file;
playing the audio file without change or after editing the audio file according to an instruction of the user to generate an output signal; and
outputting the output signal to a cosmetic device connected to an audio output terminal of the content reproduction apparatus and thereby causing the cosmetic device to perform the treatment on the user.

2. The content reproduction apparatus as claimed in claim 1, wherein the process further includes
when the content file corresponding to the set treatment is not present in the storage, accessing a predetermined content server via a communication network and obtaining the content file corresponding to the set treatment from the content server.

3. The content reproduction apparatus as claimed in claim 1, wherein the audio output terminal is a dock port.

4. The content reproduction apparatus as claimed in claim 1, wherein the editing of the audio file includes editing at least one of a duration of the audio file, an output intensity of the audio file, a play speed of the audio file, a waveform of the audio file, a number of audio files to be played, and an order in which audio files are played.

5. The content reproduction apparatus as claimed in claim 1, wherein the process further includes
obtaining a condition of a skin of the user and diagnosing the skin of the user based on the obtained condition of the skin.

6. The content reproduction apparatus as claimed in claim 1, further comprising:
a booster/constant-current device configured to increase a voltage of a waveform of the audio file and keep a current of the waveform constant.

7. The content reproduction apparatus as claimed in claim 1, wherein in the outputting, a waveform obtained by combining a waveform of the audio file and a waveform of music is output.

8. A content reproduction method performed by a content reproduction apparatus that includes a storage storing a plurality of content files and performs treatments by playing the content files stored in the storage, the content reproduction method comprising:
setting a treatment based on a treatment condition input by a user;
obtaining, from the storage, a content file that corresponds to the set treatment;
determining whether the content file includes an audio file;
when it is determined that the content file includes no audio file, converting the content file into the audio file;
playing the audio file without change or after editing the audio file according to an instruction of the user to generate an output signal; and
outputting the output signal to a cosmetic device connected to an audio output terminal of the content reproduction apparatus and thereby causing the cosmetic device to perform the treatment on the user.

9. The content reproduction method as claimed in claim 8, further comprising:
when the content file corresponding to the set treatment is not present in the storage, accessing a predetermined content server via a communication network and obtaining the content file corresponding to the set treatment from the content server.

10. The content reproduction method as claimed in claim 8, wherein the audio output terminal is a dock port.

11. The content reproduction method as claimed in claim 8, wherein the editing the audio file includes editing at least one of a duration of the audio file, an output intensity of the audio file, a play speed of the audio file, a waveform of the audio file, a number of audio files to be played, and an order in which audio files are played.

12. The content reproduction method as claimed in claim 8, further comprising:
obtaining a condition of a skin of the user and diagnosing the skin of the user based on the obtained condition of the skin.

13. The content reproduction method as claimed in claim 8, further comprising:
increasing a voltage of a waveform of the audio file and keeping a current of the waveform constant.

14. A non-transitory computer-readable storage medium storing program code for causing a computer to perform the content reproduction method of claim 8.

* * * * *